United States Patent [19]

Markwell et al.

[11] Patent Number: 5,109,000

[45] Date of Patent: Apr. 28, 1992

[54] THIOL CARBOXYLIC ACID DERIVATIVES AND THEIR USE AS COLLAGENASE INHIBITOR

[75] Inventors: Roger E. Markwell; Stephen A. Smith; Ian Hughes, all of Harlow, England

[73] Assignee: Beecham Group p.l.c., Brentford, England

[21] Appl. No.: 517,391

[22] Filed: Apr. 30, 1990

Related U.S. Application Data

[62] Division of Ser. No. 136,913, Dec. 22, 1987, abandoned.

[30] Foreign Application Priority Data

Dec. 24, 1986 [GB] United Kingdom ............ 8630928
Jul. 29, 1987 [GB] United Kingdom ............ 8717924

[51] Int. Cl.⁵ .......... A61K 31/395; A61K 31/215; A61K 31/19; C07D 295/12
[52] U.S. Cl. .......... 514/237.8; 514/255; 514/419; 514/541; 514/547; 514/548; 514/550; 514/616; 544/159; 544/400; 560/9; 560/145; 562/426; 562/556
[58] Field of Search ............ 548/495; 560/9, 145; 562/426, 556; 514/419, 541, 547, 548, 550, 616, 237.8, 255; 544/159, 400

[56] References Cited

U.S. PATENT DOCUMENTS 4,263,293  4/1981  Sundeen et al. .......... 548/495
4,595,700  6/1986  Donald et al. .......... 564/154

FOREIGN PATENT DOCUMENTS 0062003  10/1982  European Pat. Off. .......... 548/495
0185380  6/1986  European Pat. Off. .......... 548/495

2559189  7/1976  Fed. Rep. of Germany ...... 548/495

Primary Examiner—Johann Richter
Attorney, Agent, or Firm—Hopgood, Calimafde, Kalil, Blaustein & Judlowe

[57] ABSTRACT

Novel compounds of the formula (I), processes for their preparation and their use as collagenase inhibitors are described:

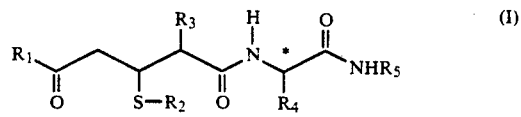

in which $R_1$ is hydroxy; alkoxy; aryloxy; aralkyloxy; $-NR_6R_7$ where $R_6$ and $R_7$ are hydrogen or alkyl, or $R_6$ and $R_7$ together with the N-atom to which they are bonded form a 5- to 7-membered ring with an optional heteroatom; $-NHCH(R_8)COR_9$ is hydrogen; alkyl optionally substituted by hydroxy, alkoxy, $-NR_6R_7$, quanidine; $CO_2H$, $CONH_2$, SH, or S-alkyl; or $CH_2-AR$ where Ar is optionally substituted aryl; and $R_9$ is hydroxy, alkoxy or $-NR_6R_7$.

$R_2$ is hydrogen or acyl.

$R_3$ is $C_{3-6}$ alkyl.

$R_4$ is hydrogen; alkyl; $-CH_2R_{10}$ where $R_{10}$ is optionally substituted phenyl or heteroaryl; or $-CH(R_{12})O-R_{11}$ where $R_{11}$ is hydrogen; alkyl; or $-CH_2Ph$ where Ph is optionally substituted phenyl; and $R_{12}$ is hydrogen or alkyl.

$R_5$ is hydrogen; alkyl; or $-CH(R_{13})COR_{14}$ where $R_{13}$ is hydrogen or alkyl; and $R_{14}$ is hydroxy, alkoxy or $-NR_6R_7$.

8 Claims, No Drawings

THIOL CARBOXYLIC ACID DERIVATIVES AND THEIR USE AS COLLAGENASE INHIBITOR

This application is a divisional of Ser. No. 136,913 filed Dec. 22, 1987 now abandoned.

The present invention relates to novel thiol-carboxylic acid derivatives, processes for their preparation and their use in medicine. In particular, the present invention relates to their use as collagenase inhibitors for treating arthritic and other diseases.

The range of therapeutic applications of the collagenase inhibitors described hereinafter reflects the fundamental role of collagen within the connective tissue matrix throughout the body, and extends to many diseases not primarily due to collagen destruction but involving tissue remodelling, as these will also be susceptible to clinical intervention with collagenase inhibitors. In particular, inhibition of collagenases released from synovial and skin fibroblasts, chondrocytes, peripheral mononuclear cells, keratinocytes and gingival tissue, as well as inhibition of collagenase stored in polymorphonuclear leucocytes (PMNLs) should be of therapeutic value, and the present compounds are envisaged as having application against these and related mammalian collagenases.

Specifically, collagenase inhibitors will provide useful treatments for arthritic diseases such as rheumatoid arthritis and osteoarthritis, soft tissue rheumatism, polychondritis and tendonitis; for bone resorption diseases such as osteoporosis, Paget's disease, hyperparathyroidism and cholesteatoma; for the recessive classes of dystrophic epidermolysis bullosa; for periodontal disease and related consequences of gingival collagenase production or of PMNL collagenase production following cellular infiltration to inflamed gingiva; for corneal ulceration e.g. that induced by alkali or other burns, by radiation, by vitamin E deficiency or retinoid deficiency; and for systemic chemotherapy of cancer, where collagenase has been implicated in the neovascularization required to support tumour survival and growth, and in the penetration of tumour cells through the basement membrane of the vascular walls during metastasis. A collagenase inhibitor may also be of use in some post-operative conditions such as colonic anastomosis in which collagenase levels are raised.

As a particular example of the therapeutic value of collagenase inhibitors, chronic arthritic diseases lead to extensive loss of the collagen and proteoglycan components within the cartilage and bone of the affected joints. Neutral metalloproteases, especially collagenases and proteoglycanases, are currently thought to be the major enzymes involved.

These enzymes have been detected in extracts of synovial and cartilage tissue, and have also been extensively studied in tissue cultures of these organs. Apart from control of the biosynthesis or secretion of the enzymes, the most significant natural regulation of the activity of collagenase and proteoglycanase in the normal and diseased state, is considered to be the production of inhibitors such as the Tissue Inhibitor of Metalloproteases (TIMP) and $\alpha_2$-macroglobulin. An imbalance between the levels of proteolytic enzymes and natural inhibitors will allow destruction of the connective tissue components to proceed.

Restoration of the enzyme-inhibitor balance by treatment with synthetic inhibitors of collagenase thus offers a useful therapy for a wide range of connective tissue diseases in which collagenolytic activity is a causative or major contributory factor.

U.S. Pat. No. 4,595,700 discloses compounds of the formula (A):

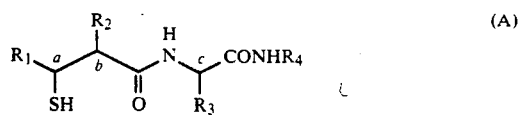

in which:

$R_1$ represents lower alkyl, phenyl or phenyl lower alkyl;
$R_2$ and $R_4$ represent lower alkyl; and
$R_3$ represents lower alkyl, benzyloxyalkyl, alkoxybenzyl or benzyloxybenzyl wherein the oxyalkyl or alkoxy moiety contains 1 to 6 carbon atoms and a, b and c represent chiral centres with optional R or S stereochemistry.

These compounds are described as inhibitors of collagenase, useful in the treatment of rheumatoid arthritis and related diseases in which collagenolytic activity is a contributing factor.

A novel class of thiol-carboxylic acid derivatives has now been discovered, which are collagenase inhibitors and thus of potential utility in the treatment of diseases in which collagenolytic activity and tissue remodelling is implicated.

According to the present invention there is provided a compound of general formula (I), or a salt, solvate or hydrate thereof:

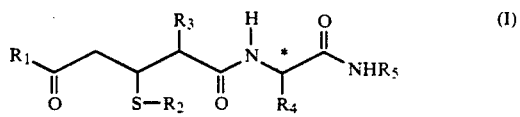

in which:

$R_1$ is —OH; alkoxy; aryloxy; aralkyloxy; —$NR_6R_7$, where each of $R_6$ and $R_7$ is hydrogen or alkyl, or $R_6$ and $R_7$ together with the nitrogen atom to which they are bonded form a 5-, 6- or 7-membered ring with an optional oxygen, sulphur or optionally substituted nitrogen atom in the ring; or a group

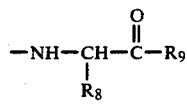

where $R_8$ is hydrogen; alkyl optionally substituted by —OH, alkoxy, —$NR_6R_7$, guanidine, —$CO_2H$, —$CONH_2$, —SH, or —S-alkyl; or —$CH_2$—Ar where Ar is optionally substituted aryl; and $R_9$ is alkoxy; —OH; or —$NR_6R_7$;

$R_2$ is hydrogen; or acyl, such as

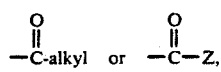

where Z is optionally substituted aryl;
$R_3$ is $C_{3-6}$ alkyl;
$R_4$ is hydrogen; alkyl; —$CH_2$—$R_{10}$ where $R_{10}$ is optionally substituted phenyl or heteroaryl; or a group

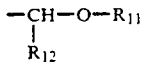

where $R_{11}$ is hydrogen; alkyl; or —CH$_2$—Ph where Ph is optionally substituted phenyl; and $R_{12}$ is hydrogen or alkyl; and $R_5$ is hydrogen; alkyl; or a group

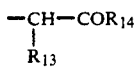

where $R_{13}$ is hydrogen; or alkyl; and $R_{14}$ is hydroxy; alkoxy; or —NR$_6$R$_7$.

Unless otherwise specified, each alkyl or alkoxy group is a $C_{1-8}$ group, more preferably $C_{1-6}$, and may be a straight chain or branched.

Optional substituents for aryl, phenyl and heteroaryl groups may be selected from OH, $C_{1-6}$ alkyl, $C_{1-6}$ alkoxy and halogen.

Examples of $R_1$ are hydroxy; $C_{1-6}$ alkoxy, such as methoxy, ethoxy or t-butyloxy; benzyloxy; and —NR$_6$R$_7$ in which R$_6$ is hydrogen, and R$_7$ is hydrogen or $C_{1-8}$ alkyl such as methyl or ethyl; or —NR$_6$R$_7$ is N'-methyl-N-piperazinyl or N-morpholinyl. Other examples of $R_1$ are —NH—CH$_2$—COOH, —NH—CH$_2$—CONH$_2$, —NH—CH$_2$—CO$_2$Et, —NH—CH$_2$—CO$_2$tBu,

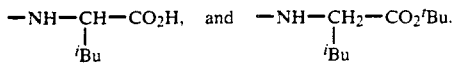

$R_1$ is preferably alkoxy, such as $C_{1-4}$ alkoxy, especially methoxy; amino; alkylamino, especially methylamino or —NH—CH$_2$—CO$_2$H.

When $R_2$ is

Z is preferably an optionally substituted phenyl group.
Examples of $R_2$ are hydrogen,

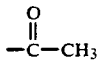

and benzoyl.

$R_3$ is preferably a $C_4$ alkyl group, such as n-butyl, iso-butyl or sec-butyl, especially iso-butyl.

When $R_4$ is —CH$_2$—R$_{10}$ and $R_{10}$ is heteroaryl, values for $R_{10}$ include 5- or 6- membered monocyclic and 9- or 10-membered bicyclic heteroaryl of which 9- or 10-membered bicyclic heteroaryl is preferred.

In addition, 5- or 6- membered monocyclic and 9- or 10-membered bicyclic heteroaryl preferably contain one or two heteroatoms selected from nitrogen, oxygen and sulphur which in the case of there being more than one heteroatom may be the same or different. When $R_{10}$ is 9- or 10- membered bicyclic heteroaryl the two rings are preferably fused with one 5- or 6- membered ring containing a single heteroatom.

$R_4$ is preferably iso-butyl; benzyl; or $C_{1-6}$ alkoxybenzyl, such as 4-methoxybenzyl;

1-(benzyloxy)ethyl or 9- or 10- membered fused bicyclic heteroarylmethyl such as 3-indolylmethyl.

Examples of $R_5$ include hydrogen; alkyl, such as methyl or ethyl, preferably methyl; and 1-(methoxycarbonyl)ethyl.

The compounds of formula (I) may form salts with bases e.g. sodium hydroxide. When a basic nitrogen atom is present, the compounds of formula (I) may form acid addition salts e.g. with hydrochloric acid. Such compounds form part of the present invention.

Where compounds of formula (I), or salts thereof, form solvates such as hydrates, these also form an aspect of the invention.

The compounds of formula (I) have at least one asymmetric centre and therefore exist in more than one stereoisomeric form. The invention extends to all such forms and to mixtures thereof, including racemates, and diastereoisomeric mixtures.

Preferred isomers are those having the S configuration at the chiral centre marked with an asterisk in formula (I).

The compounds of formula I or their salts, solvates or hydrates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% by weight, preferably 75%, more preferably 90% and still more preferably 95% or 99% or more of the compound of formula I or its salt or solvate.

One preferred pharmaceutically acceptable form is the crystalline form.

The present invention provides the compounds of formula (I) or pharmaceutically acceptable salts or solvates thereof for use as active therapeutic agents, particularly as agents for treatment of musculo-skeletal disorders resulting from collagenolytic activity, particularly arthritic diseases, and tissue remodelling, and also for the systemic chemotherapy of cancer.

The present invention also provides a process for the preparation of a compound of formula (I) in which $R_2$ is hydrogen, which comprises cleaving a group L from a compound of formula (II):

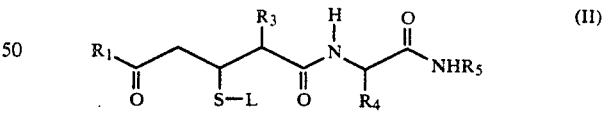

wherein L is $L_1$ which is a conventional sulphur protecting group or $L_2$ which is a group R—S— where R is any organic residue such that the group R—S— provides a cleavable disulphide bond, and $R_1$, $R_3$, $R_4$ and $R_5$ are as defined for formula (I).

Typically a protecting group $L_1$ is a substituted benzyl group, such as alkoxybenzyl e.g. 4-methoxybenzyl or an aliphatic or aryl acyl group such as acetyl or benzoyl. When $L_1$ is acyl it is of course identical to $R_2$, so these compounds of formula (II) are themselves compounds of the invention. When L is R—S— then typically the compound of formula (II) is a dimer of the compound of formula (I) in which $R_2$ is hydrogen.

When L is $L_1$, and $L_1$ is a substituted benzyl sulphur protecting group, such as 4-methoxy benzyl, then $L_1$ may be removed by treatment with mercury acetate in trifluoroacetic acid containing anisole followed by reaction with hydrogen sulphide in dimethyl formamide, in a procedure analogous to that described in Chem. Pharm. Bull 1957, 26, 1576.

When $L_1$ is an acyl group it may be removed by treatment with a base, for example aqueous ammonia or dilute aqueous sodium hydroxide, or by treatment with an acid, for example methanolic hydrochloric acid.

When L is $L_2$ the dimerized compound may be split at the disulphide link by treatment with zinc and hydrochloric acid or by passing hydrogen sulphide through the solution.

Other conventional methods for removing sulphur protecting groups or cleaving disulphide bridges may also be used.

Compounds of formula (II) in which L is $L_1$ may be prepared by treating a compound of formula (III):

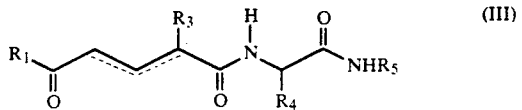

in which $R_1$, $R_3$, $R_4$ and $R_5$ are as defined in formula (I) with a thiol of formula (IV):

$$L_1-SH \qquad (IV)$$

in which $L_1$ is as defined in formula (II). When $L_1$ is $R_2$, the compounds of formula (II) thereby produced are compounds of the invention.

Compounds of formula (II) may also be prepared by treating a compound of formula (V):

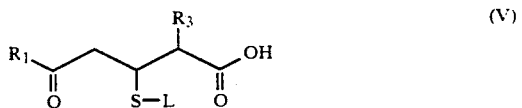

in which L, $R_1$ and $R_3$ are as defined in formula (II), with a compound of formula (VI):

in which $R_4$ and $R_5$ are as defined in formula (I).

The reaction is preferably carried out in the presence of a coupling agent, such as N,N-dicyclohexylcarbodiimide.

Compounds of formula (II) in which L is $L_2$ may also be prepared by oxidative coupling, with iodine or oxygen, of a compound of formula (I) in which $R_2$ is hydrogen.

Compounds of formula (II) can be converted to further compounds of formula (II) while retaining the same group L, which group in turn can be cleaved to form compounds of the invention in which $R_2$ is hydrogen.

For example, those compounds of formula (II) in which $R_1$ is —OH may be prepared under acid conditions by hydrolysis of compounds in which $R_1$ is alkoxy, aryloxy or aralkyloxy or by hydrogenolysis of compounds in which $R_1$ is benzyloxy or substituted benzyloxy in the presence of a catalyst such as palladium black.

Those compounds of formula (II) in which $R_1$ is $-NR_6R_7$ may be prepared from compounds in which $R_1$ is —OH by treating the latter compounds with an amine of formula $NHR_6R_7$ in the presence of a coupling agent such as N,N-dicyclohexylcarbodiimide or N-ethyl-N'-dimethylaminopropylcarbodiimide.

Compounds of formula (II) in which $R_1$ is —NH—CH($R_8$)—COR$_9$ may be similarly prepared from compounds in which $R_1$ is OH by treatment with amine derivatives of formula $NH_2CH(R_8)COR_9$ where $R_9$ is an alkoxy or amine group, followed by hydrolysis to give an $R_9$ hydroxy group, if desired.

In addition, compounds of the invention in which $R_2$ is acyl can be converted to further compounds of the invention with concomitant cleavage of the acyl group to give compounds of formula (I) in which $R_2$ is hydrogen.

For example, those compounds of formula (I) in which $R_1$ is OH and $R_2$ is hydrogen may be prepared by hydrolysis of compounds in which $R_1$ is alkoxy, aryloxy or aralkyloxy and $R_2$ is acyl under basic conditions such as treatment with dilute sodium hydroxide.

The intermediate compounds of formula (III) may be prepared by treating a compound of formula (VII):

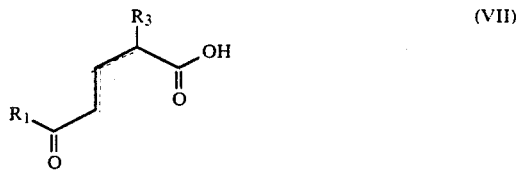

in which $R_1$ and $R_3$ are as defined in formula (I), with a compound of formula (VI) as defined above.

The thiols of formula (IV) are known compounds.

The intermediate compounds of formula (V) may be prepared by treating a compound of formula (VII), as defined above, with a thiol of formula (IV).

It may be necessary or convenient to protect the carboxyl function in compounds of formula (VII), for example by esterification, prior to treatment with the thiol of formula (IV) and subsequently remove the protecting group under acid conditions.

The compounds of formula (VI) are either known amino acid derivatives or can be made from these derivatives by known methods.

The intermediates of formulae (III), (V) and (VII) disclosed herein are in some forms novel compounds and form an aspect of the present invention as do the described processes for their preparation.

The preparation of certain compounds of formula (VII) is illustrated in the following reaction Scheme I, using compounds in which $R_3$ is iso-butyl.

The starting material, compound A in Scheme I is a known compound, diethyl 3-oxopentanedioate.

The preparation of compounds of formula (V) from compounds of formula (VII) in which the carboxyl group is protected as described above is illustrated in reaction Scheme 2, using compounds in which $R_1$ is methylamino, $R_3$ is iso butyl, L is benzoyl and the carboxyl group is protected as a t-butyl ester.

SCHEME 1
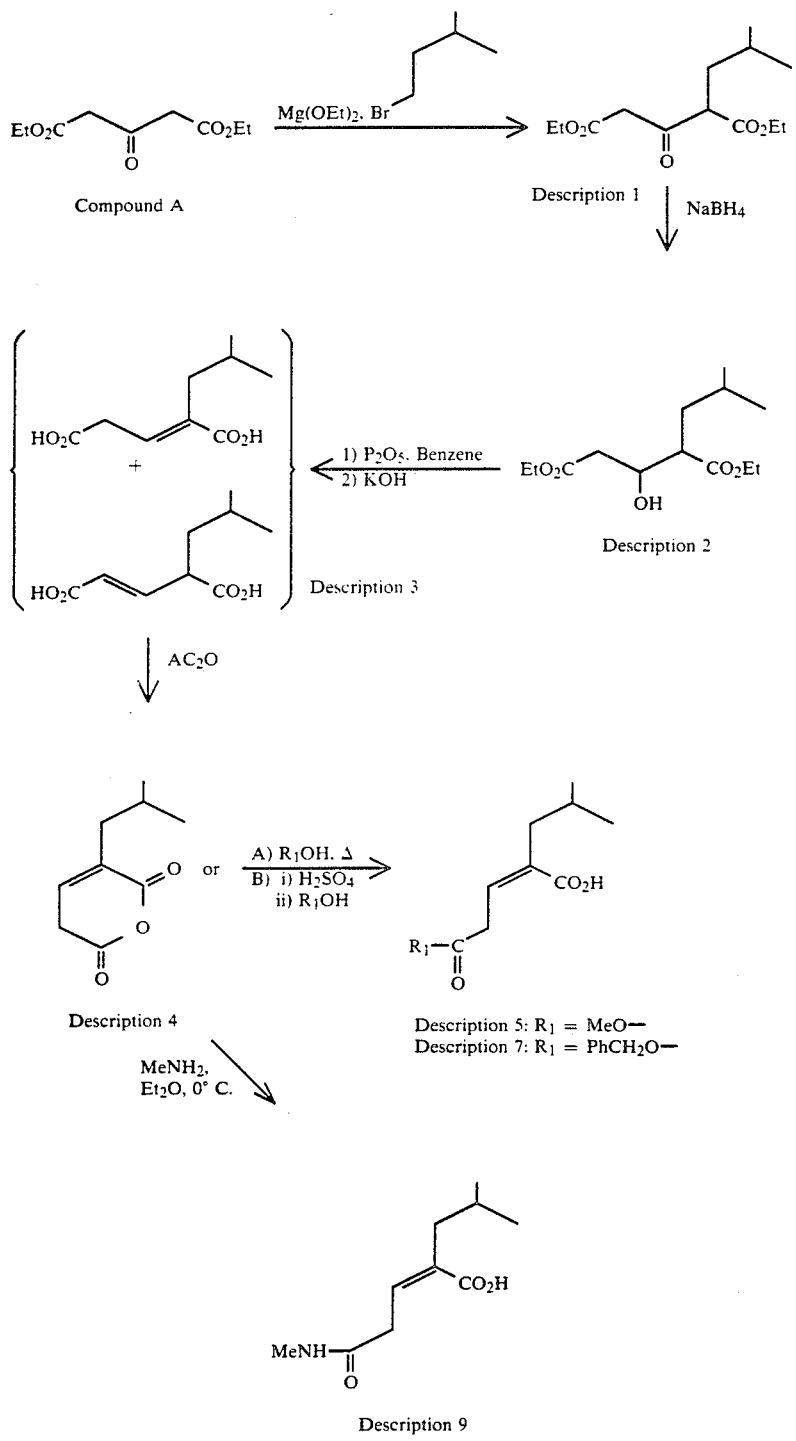

SCHEME 2

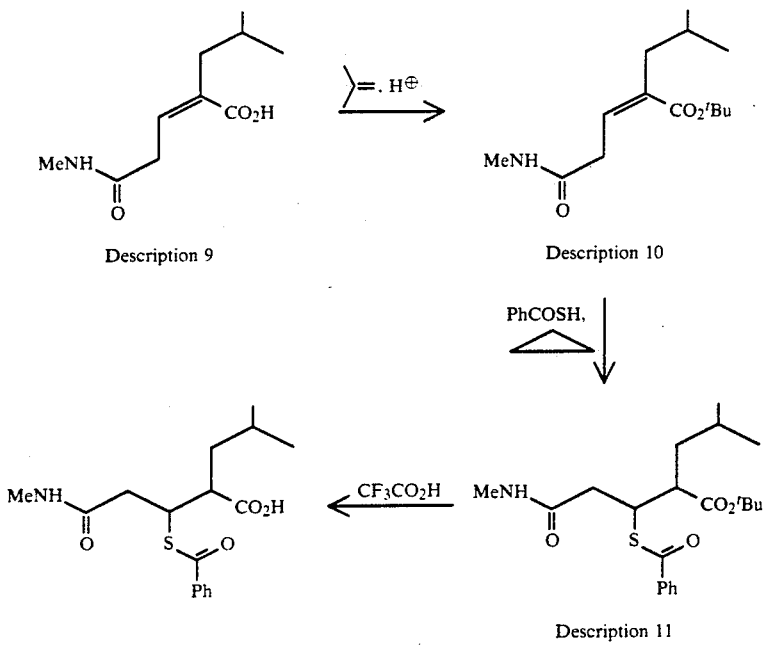

Where obtainable, pharmaceutically acceptable salts of the compounds of formula (I) may be formed conventionally by reaction with the appropriate acid or base. Solvates may be formed by crystallization from the appropriate solvent.

As mentioned previously, the compounds of formula (I) exist in more than one diastereoisomeric form. Where the processes of the invention produce mixtures thereof, the individual isomers may be separated one from another by chromatography, e.g. HPLC.

Alternatively, separate diastereoisomeric compounds of formula (I) can be obtained by using stereoisomerically pure starting materials or by separating desired isomers of intermediates at any stage in the overall synthetic process, and converting these intermediates to compounds of formula (I).

The present invention further provides a pharmaceutical composition, which comprises a compound of formula (I),or a pharmaceutically acceptable salt, solvate or hydrate thereof, and a pharmaceutically acceptable carrier.

A composition of this invention is useful in the treatment of rheumatism and arthritis and in the treatment of other collagenolytic conditions.

A composition of the invention, which may be prepared by admixture, may contain a diluent, binder, filler, disintegrant, flavouring agent, colouring agent, lubricant or preservative in conventional manner. These conventional excipients may be employed in conventional manner, for example as in the preparation of compositions of related peptide enzyme inhibitors, such as the ACE inhibitor captopril.

A composition of the invention may be adapted for oral, topical, percutaneous, rectal or parenteral-intravenous, intramuscular, sub-cutaneous, intradermal or intra-articular administration, but oral administration is preferred.

Preferably, a pharmaceutical composition of the invention is in unit dosage form and in a form adapted for use in the medical or veterinarial fields. For example, such preparations may be in a pack form accompanied by written or printed instructions for use as an agent in the treatment or prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen.

The compound or composition of the invention may be formulated for administration by any route, the preferred route depending upon the disorder for which treatment is required, and is preferably in unit dosage form or in a form that a human patient may administer to himself in a single dosage.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients. For example, in a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository or for parenteral administration in an injectable form. For injection, the compounds of the invention may be presented in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers or solutes to render the solution isotonic with the blood, thickening agents, suspending agents or other pharmaceutically acceptable additives. Such forms will be presented in sterile unit dose form such as ampoules or disposable injection devices or in multi- dose forms such as a bottle from which the appropriate dose may be withdrawn or a solid form or concentrate which can be used to prepare an injectable formulation.

For topical and percutaneous administration, the preparations may also be presented as an ointment, cream, lotion, gel, spray, aerosol, wash or skin paint or patch.

A unit dose for inflammatory diseases will generally contain from 10 to 1000 mg and preferably will contain from 10 to 500 mg, in particular 10, 50, 100, 150, 200, 250, 300, 350, 400, 450 or 500 mg. The composition may be administered once or more times a day, for example 2, 3 or 4 times daily, so that the total daily dose for a 70 kg adult will normally be in the range 10 to 3000 mg. Alternatively, in particular for injection, the unit dose will contain from 2 to 200 mg of a compound of the invention and be administered in multiples, if desired, to give the desired daily dose.

The present invention additionally provides a method of treating a collagenolytic condition such as rheumatism and/or arthritic conditions, or cancer, or other diseases in which enzyme-mediated breakdown of connective tissue components plays a role in mammals, such as humans, which comprises administering an effective amount of a compound of formula (I) or a pharmaceutically acceptable salt, solvate or hydrate thereof, to the mammal.

The present invention also provides the use of a compound of formula (I) or a pharmaceutically acceptable salt, solvate or hydrate thereof, for the manufacture of a medicament for use as an active therapeutic substance, particularly in the treatment of collagenolytic conditions, such as rheumatism, cancer, bone disorders, skin diseases, periodontal disease or corneal ulceration, in mammals.

The following Descriptions and Examples illustrate the preparation of compounds of the invention and the subsequent biological data illustrates their pharmacological activity. All temperatures are expressed in °C.

DESCRIPTION 1

Diethyl 2-(2-methylpropyl)-3-oxopentanedioate (D1)

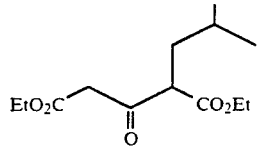

Diethyl 3-oxopentanedioate (45.5 ml, 0.25 mol) was added to a suspension of magnesium ethoxide (prepared from magnesium turnings (9 g, 0.375 mol) and iodine (0.1 g) in dry ethanol (275 ml)), and the mixture was heated under reflux for 90 min. 1-Bromo-2-methylpropane (54 ml, 0.5 mol) was added, and the reaction was heated under reflux for 16 h. Further 1-bromo-2-methylpropane (27 ml, 0.25 mol) was added to the boiling mixture, and after 3 h the solvent was evaporated in vacuo. The residue was partitioned between 2 N hydrochloric acid and ether. After extracting the aqueous phase with ether, the combined organics were washed successively with water, 5% sodium bicarbonate, water and brine, then were dried ($Na_2SO_4$) and evaporated in vacuo. The residue was distilled to give the title compound as a colourless oil (40 g, 62%), bp 118°–120° C. (1 mmHg). δ ($CDCl_3$): 0.9 (6H, d, J=6Hz), 1.25 (6H, t, J=7Hz), 1.4–1.9 (3H, m), 3.5 (2H, s), 3.7 (1H, d, J=9Hz) and 4.2 (4H, q, J=7Hz).

DESCRIPTION 2

Diethyl 3-hydroxy-2-(2-methylpropyl)pentanedioate (D2)

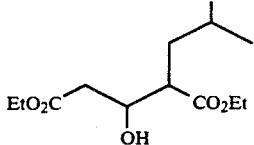

Sodium borohydride (1.1 g, 29 mmol) was added to an ice-cold solution of diethyl 2-(2-methylpropyl)-3-oxopentanedioate (7.5 g, 29 mmol) in ethanol (75 ml). The mixture was stirred at 5°–10° C. for 2 h, then 2 N hydrochloric acid (18 ml) was added slowly at 0° C., and the mixture was stirred at room temperature for 45 min. The mixture was diluted with water (400 ml), then was extracted with ethyl acetate (4×100 ml). The extracts were washed with water (2×100 ml) and brine (100 ml), then were dried (Na$_2$SO$_4$) and evaporated in vacuo to leave the title compound as an oil (7.5 g, 100%).

δ (CDCl$_3$): 0.9 (6H, d, J=5Hz), 1.15 (6H, t, J=7Hz), 1.1–1.8 (3H, m), 2.2–2.7 (3H, m), 3.3 (1H, brs), 3.7–4.1 (1H, m) and 4.1 (4H, q, J=7Hz).

DESCRIPTION 3

2- and 4-(2-Methylpropyl)pent-2-enedioic acids (D3)

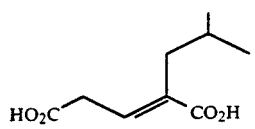

(D3)

and

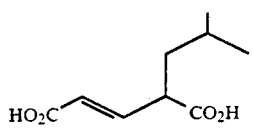

Diethyl 3-hydroxy-2-(2-methylpropyl)pentanedioate (26 g, 100 mmol) was added to a stirred suspension of phosphorus pentoxide (21.3 g, 150 mmol) in dry benzene (220 ml), and the mixture was heated under reflux for 3 h. Water (200 ml) was added to the cooled mixture to break down the brown gum. The layers were separated and the aqueous phase was extracted with ether (4×150 ml). The combined organics were washed with water (150 ml) and brine (300 ml), then were dried (Na$_2$SO$_4$) and evaporated in vacuo to leave a brown oil.

The above oil was dissolved in a solution of potassium hydroxide (16.8 g, 300 mmol) in 80% ethanol (300 ml), and the mixture was heated under reflux for 3 h. The ethanol was evaporated in vacuo and the residue was diluted with water (400 ml), and washed with ether (150 ml). The aqueous solution was acidified with 5 N hydrochloric acid, then was extracted with ether (4×150 ml). The combined extracts were washed with brine (2×100 ml), then were dried (Na$_2$SO$_4$) and evaporated in vacuo to leave a mixture of the two title compounds as an oil which slowly solidified (14.3 g, 77%). The mixture of acids was used in the following stage without separation.

However, it was possible to separate the isomers by crystallisation from ether/pentane, which gave 2-(2-methylpropyl)pent-2-enedioic acid as a solid, m.p. 129°–135° C. (chloroform).

δ (DMSO d6): 0.9 (6H, d, J=6Hz), 1.3–2.0 (1H, m), 2.15 (2H, d, J=7Hz), 3.2 (2H, d, J=7Hz), and 6.8 (1H, t, J=7Hz).

Evaporation of the mother liquors gave 4-(2-methylpropyl)pent-2-enedioic acid as an oil.

δ (CDCl$_3$): 0.9 (6H, d, J=6Hz), 1.4–2.3 (3H, m), 3.4 (1H, m), 5.85 (1H, d, J=15Hz) and 7.0 (1H, dd, J=15, 7Hz).

DESCRIPTION 4

2-(2-Methylpropyl)pent-2-enedicarboxylic anhydride (D4)

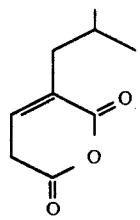

(D4)

A mixture of 2- and 4-(2-methylpropyl)pent-2-enedioic acids (14.3 g, 77 mmol) in acetic anhydride (40 ml) was heated under reflux for 2½ h. The acetic anhydride was evaporated in vacuo to leave a brown oil, which was distilled to give the title compound as a low-melting yellow solid (5.8 g, 45%), b.p. 145°–155° C. (5 mmHg).

δ (CDCl$_3$): 0.9 (6H, d, J=6Hz), 1.5–2.4 (3H, m), 3.5 (2H, brd, J=4Hz), 6.5 (1H, t, J=4Hz).

DESCRIPTION 5

4-Methoxycarbonyl-2-(2-methylpropyl)but-2-enoic acid (D5)

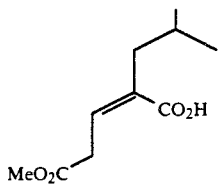

(D5)

2-(2-Methylpropyl)pent-2-enedicarboxylic anhydride (960 mg, 5.7 mmol) was dissolved in concentrated sulphuric acid (10 ml), then immediately poured into ice-cooled methanol (50 ml). The solution was diluted with water (100 ml) and was extracted with ether (3×50 ml). The extracts were washed with brine, then dried (MgSO$_4$) and the solvent was evaporated in vacuo to leave the title compound as a pale yellow solid (960 mg, 84%), mp 40°–45° C. (hexane).

δ (CDCl$_3$): 0.9 (6H, d, J=6Hz), 1.4–2.0 (1H, m), 2.2 (2H, d, J=6Hz), 3.55 (2H, d, J=7Hz), 6.2 (1H, t, J=7Hz) and 9.6 (1H, brs).

ν$_{max}$ (nujol): 1735, 1690 and 1635 cm$^{-1}$.

DESCRIPTION 6

6-Methyl-4-[[[1-[(methylamino)carbonyl]-2-(4-methoxyphenyl)ethyl]amino]carbonyl]hept-3-enoic acid, methyl ester (D6)

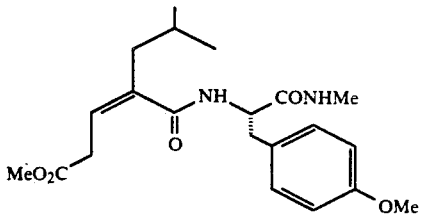

(D6)

N,N-Dicyclohexylcarbodiimide (515 mg. 2.5 mmol) was added to an ice-cooled solution of 4-methoxycarbonyl-2-(2-methylpropyl)but-2-enoic acid (500 mg. 2.5 mmol) and O-methyl-L-tyrosine N-methylamide (520 mg. 2.5 mmol) in dry dichloromethane (30 ml), and the mixture was stirred at room temperature for 18 h. The precipitated solid was filtered off and washed with a little dichloromethane, then the organic solution was washed successively with 1 N hydrochloric acid (20 ml), 1 N sodium bicarbonate (20 ml), and water. The solution was dried (MgSO4) and evaporated in vacuo. Column chromatography (30 g silica) of the residual solid, eluting with 5% methanol/dichloromethane gave the title compound (520 mg, 53%), m.p. 142°–144° C. (dichloromethane/pentane).

δ (CDCl3): 0.82 (3H, d, J=7Hz), 0.83 (3H, d, J=7Hz), 1.58 (1H, m), 2.18 (2H, d, J=7Hz), 2.72 (3H, d, J=5Hz), 3.02 (2H, m), 3.16 (2H, d, J=7Hz), 3.70 (3H, s), 3.78 (3H, s), 4.57 (1H, m), 5.70 (1H, brs), 6.32 (1H, t, J=7Hz), 6.45 (1H, d, J=8Hz), 6.83 (2H, d, J=8Hz) and 7.12 (2H, d, J=8Hz).

DESCRIPTION 7

4-Benzyloxycarbonyl-2-(2-methylpropyl)but-2-enoic acid (D7)

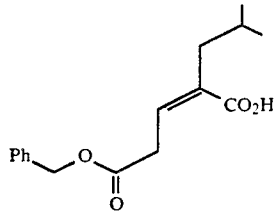

(D7)

The title compound was prepared in 91% yield from benzyl alcohol by the method of D5.

A sample recrystallized from ether/pentane gave white needles, m.p. 72–73.5. (Found: C, 69.55; H, 7.38. C16H20O4 requires C, 69.54; H, 7.30%).

δ (CDCl3): 0.9 (6H, d, J=6Hz), 1.4–2.0 (1H, m), 2.16 (2H, d, J=6Hz), 3.63 (2H, d, J=7Hz), 5.08 (2H, s), 6.23 (1H, t, J=7Hz) and 7.2 (5H, s).

DESCRIPTION 8

6-Methyl-4-[[[1-(S)-[(methylamino)carbonyl]-2-(4-methoxyphenyl)ethyl]amino]carbonyl]hept-2(and 3)-enoic acids, benzyl esters (D8)

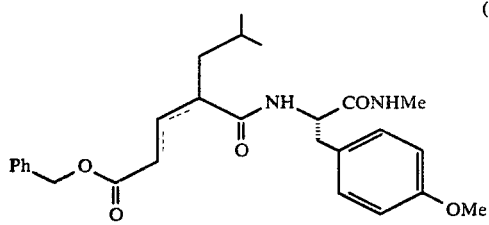

(D8)

The benzyl ester (D7) (26.46 g, 0.096 mole) in dry acetonitrile (500 ml) under N2 was cooled to 0° in an ice bath and treated with 1,1,-carbonyldiimidazole (15.69 g, 0.096 mole) in one portion. After 1 h at 0°, a solution of O-methyl-L-tyrosine N-methylamide (20 g, 0.096 mole) in dry acetonitrile (200 ml) was added dropwise with stirring. On completing the addition the mixture was maintained at 0° for 1 h and then allowed to warm to room temperature. Stirring was continued overnight and then solvent was removed in vacuo and the residue taken up in ethyl acetate. After washing with 1 N HCl (2×200 ml) and extracting the combined aqueous layers with ethyl acetate (3×100 ml), the combined organic layers were washed with water (100 ml), dried with anhydrous MgSO4, filtered and evaporated to dryness to give a red oil. Purification by chromatography on silica gel with chloroform followed by 2% methanol/chloroform gave the title compounds as a yellow gum (41.01 g, 92%). Recrystallization of a sample from ethyl acetate/pentane gave a white crystalline product, m.p. 98°–101°. (Found: C, 69.38; H, 7.50; N, 5.73. C27H34N2O5 requires C, 69.51; H, 7.34; N, 6.00%).

DESCRIPTION 9

4-Methylaminocarbonyl-2-(2-methylpropyl)but-2-enoic acid (D9)

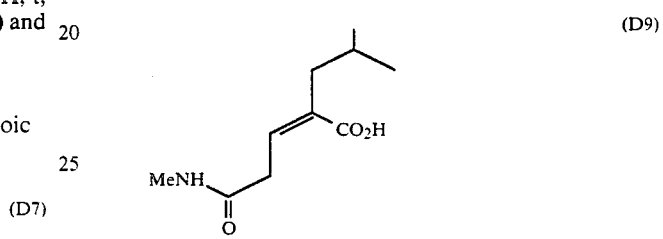

(D9)

A slow stream of anhydrous methylamine was passed into a solution of 2-(2-methylpropyl)pent-2-ene dicarboxylic anhydride (1.3 g) in dry ether (25 ml) at 0° C. After 1 h the methylamine source was removed and the solution was evaporated to dryness in vacuo. The residue was dissolved in ethyl acetate and extracted with 10% aqueous sodium carbonate. The aqueous phase was acidified with dilute hydrochloric acid and re-extracted with ethyl acetate. The extracts were washed with water, dried (MgSO4), and evaporated to dryness to leave the title compound as a white solid (0.75 g, 49%), m.p. 120°–122° C., after trituration with ether; (Found: C, 60.4; H, 8.5; N, 6.95. C10H17NO3 requires C, 60.3; H, 8.6; N, 7.05%).

δ (d6-DMSO): 0.85 (6H, d, J=8Hz), 1.75 (1H, m), 2.15 (2H, d, J=6Hz), 2.7 (3H, d, J=5Hz), 3.3 (2H, d, J=8Hz), 6.05 (1H, t, J=8Hz), 7.8 (1H, brs) and 12.4 (1H, brs).

DESCRIPTION 10

4-Methylaminocarbonyl-2-(2-methylpropyl)but-2-enoic acid, tert-butyl ester (D10)

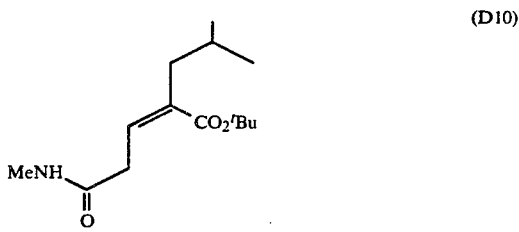

(D10)

A suspension of 4-methylaminocarbonyl-2-(2-methylpropyl)but-2-enoic acid (2.4 g) in chloroform (35 ml) was treated with an excess of isobutylene (30 ml) and concentrated sulphuric acid (3 drops) was added as catalyst. The mixture was stirred at room temperature in a sealed vessel for 8 days. The product was purified by silica gel chromatography [chloroformpentane (1:1) as eluant] to give the title compound (2.5 g, 81%), m.p. 35°-36° C. (pentane).

δ (CDCl₃): 0.85 (6H, d, J=8Hz), 1.5 (9H, s), 1.7 (1H, m), 2.1 (2H, d, J=8Hz), 2.8 (2H, d, J=6Hz), 3.2 (2H, d, J=10Hz), 5.9 (1H, t, J=10Hz) and 6.5 (1H, brs).

DESCRIPTION 11

2-(1-Benzoylmercapto-2-[methylaminocarbonyl]ethyl)-4-methylpentanoic acid, tert-butyl ester (D11)

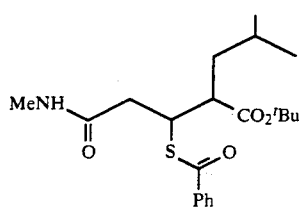

(D11)

A mixture of 4-methylaminocarbonyl-2-(2-methylpropyl)-but-2-enoic acid, tert-butyl ester (1.25 g, 4.9 mmol) and thiobenzoic acid (1.3 g, 9.4 mmol) was heated at 80° C. under nitrogen for 48 h. The product was chromatographed on neutral alumina (50 g) using chloroform as the eluant to give a foam (0.5 g) containing the title compound as the major constituent.

δ (CDCl₃): 0.9 (m), 1.45 (m), 1.65 (m), 2.6 (m), 2.8 (d, J=5Hz), 2.82 (d, J=5Hz), 3.0 (m), 3.2 (m), 4.3 (m), 5.9 (m), 7.4 (m), 7.55 (m) and 7.95 (m). Observed FAB (M+H)⁺ 394. C₂₁H₃₁NO₄S requires M 393.

DESCRIPTION 12

6-Methyl-4-[[[1-(S)-[(methylamino)carbonyl]-2-phenyl ethyl]-amino]carbonyl]hept-2(and 3)-enoic acid, methyl ester (D12)

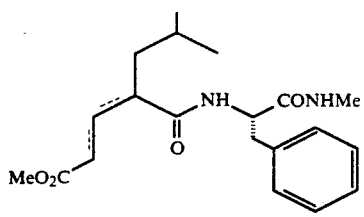

(D12)

Prepared from 4-methoxycarbonyl-2-(2-methylpropyl)but-2-enoic acid (2.0 g, 10 mmol) and L-phenylalanine-N-methylamide (1.87 g, 10.5 mmol) as described for Description 8. The product was chromatographed on silica gel with methanol-dichloromethane (1:24) as the eluant to give the title compound (2.5 g, 69%) as a foam m.p. 78°-83° C. (Found: C, 66.7; H, 8.2; N, 7.6. C₂₀H₂₈N₂O₄ requires C, 66.65; H, 7.85; N, 7.75%).

DESCRIPTION 13

6-Methyl-4-[[[1-(S)-[(methylamino)carbonyl]-2-(4-methoxyphenyl)ethyl]amino]carbonyl]hept-3-enoic acid (D13)

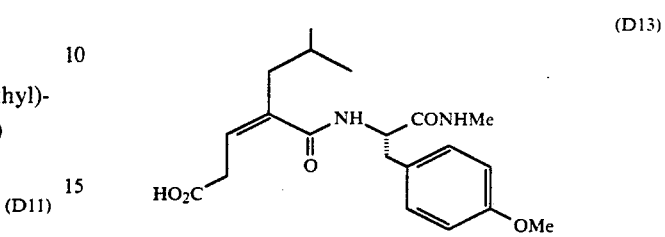

(D13)

A solution of the methyl ester (D6; 7.2 g) in methanol (80 ml) was treated with sodium hydroxide (1.1 g) in water (20 ml) and the solution was stirred at room temperature overnight. The solution was diluted with water, the methanol was removed in vacuo and the aqueous solution was washed with ethyl acetate. The aqueous solution was acidified with 5 NHCl and extracted with ethyl acetate (3×50 ml). The combined organic extracts were dried (Na₂SO₄), filtered, and the solvent evaporated in vacuo to give the title compound as a foam (6.6 g).

DESCRIPTION 14

6-Methyl-4-[[[1-(S)-[(methylamino)carbonyl]-2-(4-methoxyphenyl)ethyl]amino]carbonyl]hept-2(and 3)-enoic acid, tert-butyl ester (D14)

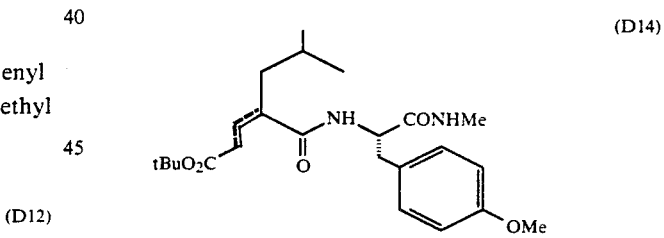

(D14)

A solution of 6-methyl-4-[[[1-(S)-[(methylamino)carbonyl]-2-(4-methoxyphenyl)ethyl]amino]carbonyl]-hept-3-enoic acid (D13; 6.6 g) in dichloromethane (50 ml) and excess of isobutylene were placed in a sealed vessel with concentrated sulphuric acid for 7 days. After washing with 10% sodium carbonate solution, followed by water, the organic extracts were dried (Na₂SO₄), filtered and evaporated to dryness to give a red oil (4.1 g). Column chromatography on silica gel, eluting with 10% methanol/chloroform gave the title compound as a foam (3.2 g).

(Found: C,66.51; H,8.31; N,6.37. C₂₄H₃₆N₂O₅ requires: C,66.64; H,8.39; N,6.48%).

Observed FAB (M+H)⁺ 433 C₂₄H₃₆N₂O₅ requires M 432.

DESCRIPTION 15

6-Methyl-4-[[[2-(R)-benzyloxy-1-(S)-[(methylamino)-carbonyl]propyl]amino]carbonyl]hept-2(and 3)-enoic acids, methyl esters (D15)

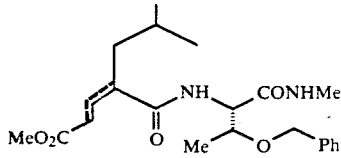

(D15)

The methyl ester (D5; 3.1 g) in dry acetonitrile (75 ml) under N₂, was cooled to 0° in an ice bath and treated with 1,1′-carbonyldiimidazole (2.74 g) in one portion. After 1 h at 0°, a solution of O-benzyl-L-threonine N-methylamide (3.44 g) in dry acetonitrile (25 ml) was added dropwise. The solution was stirred at room temperature overnight, the solvent removed in vacuo and the residue taken up in ethyl acetate. After washing with 1 N HCl (2×25 ml) and extracting the combined aqueous layers with ethyl acetate (3×50 ml), the combined organic layers were washed with water (50 ml), dried (Na₂SO₄), filtered and evaporated to dryness to give an oil. Purification by chromatography on silica gel, eluting with chloroform, followed by 5% methanol/chloroform gave the title compounds as a foam (4.4 g).

(Found: C,65.51; H,8.03; N,6.80. C₂₂H₃₂N₂O₅ requires C,65.32; H,7.97; N,6.92%).

DESCRIPTION 16

6-Methyl-4-[[[1-(S)-[(methylamino)carbonyl]-2-(3-indolyl)ethyl]amino]carbonyl]hept-2(and 3)-enoic acid, methyl ester (D16)

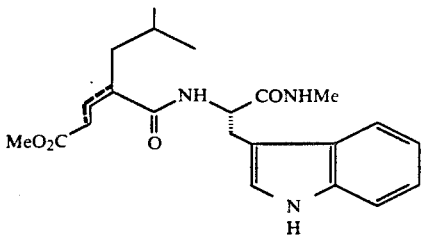

(D16)

Prepared from 4-methoxycarbonyl-2-(2-methylpropyl) but-2-enoic acid (1.75 g, 8.75 mmol) and L-tryptophan-N-methylamide (2.64 g, 13 mmol) as described for Description 8. The product was chromatographed on silica gel with methanol-chloroform (1:99) as the eluant to give the title compound (2.8 g, 80%) as a foam m.p. 60°-65° C.

(Found: C,66.07; H,7.37; N,10.53. C₂₂H₂₉N₃O₄ requires C,66.14; H,7.32; N,10.52%).

EXAMPLE 1

3-Acetylmercapto-6-methyl-4-[[[1-(S)-[(methylamino)-carbonyl]-2-(4-methoxyphenyl)ethyl]amino]carbonyl]-heptanoic acid, methyl ester (E1)

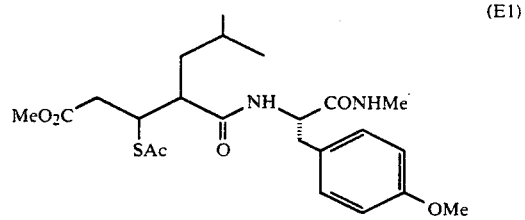

(E1)

A solution of 6-methyl-4-[[[1-(S)-[(methylamino)-carbonyl]-2-(4-methoxyphenyl)ethyl]amino]carbonyl]-hept-3-enoic acid, methyl ester (D6; 500 mg, 1.3 mmol) in thiolacetic acid (3 ml) was stirred at room temperature for 14 days, then was evaporated to dryness in vacuo. Column chromatography (30 g silica) of the residue, eluting with 10 to 25% ethyl acetate/dichloromethane gave the title compound (100 mg, 17%) m.p. 118°-135° C. Observed mass 466.2137; C₂₃H₂₄N₂O₆S requires 466.2136 Preparative HPLC (Lichrosorb diol), eluting with 20/80 (1% methanol/dichloromethane)/hexane gave two single isomers of the title compound.

Isomer A, mp 162°-165° C. had the longer retention time.

δ (CDCl₃): 0.85 (3H, d, J=7Hz), 0.87 (3H, d, J=7Hz), 1.2-1.7 (m), 2.31 (3H, s), 2.45 (1H, dd, J=8, 17Hz), 2.63 (1H, dd, J=5, 17Hz), 2.6 (1H, m), 2.71 (3H, d, J=5Hz), 2.95 (1H, dd, J=7, 14Hz), 3.03 (1H, dd, J=7, 14Hz), 3.78 (3H, s), 3.66 (3H, s), 3.89 (1H, m), 4.55 (1H, q, J=8Hz), 5.58 (1H, brd), 6.33 (1H, d, J=8Hz), 6.83 (2H, d, J=9Hz) and 7.14 (2H, d, J=9Hz).

Isomer B, mp 116°-118° C. had the shorter retention time.

δ (CDCl₃): 0.84 (3H, d, J=7Hz), 0.86 (3H, d, J=7Hz), 1.2-1.7 (m), 2.32 (3H, s), 2.49 (2H, d, J=7Hz), 2.7 (1H, m), 2.72 (3H, d, J=5Hz), 2.97 (1H, dd, J=7, 14Hz), 3.04 (1H, dd, J=7, 14Hz), 3.78 (3H, s), 3.66 (3H, s), 3.97 (1H, m), 4.52 (1H, q, J=8Hz), 5.67 (1H, brs), 6.43 (1H, d, J=8Hz), 6.83 (2H, d, J=9Hz) and 7.15 (2H, d, J=9Hz).

EXAMPLE 2

3-Mercapto-6-methyl-4-[[[1-(S)-[(methylamino)carbonyl]2-(4-methoxyphenyl)ethyl]amino]carbonyl]heptanoic acid methyl ester (E2)

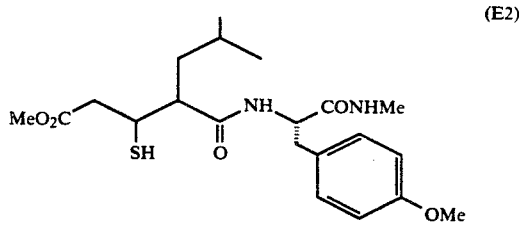

(E2)

An ice-cooled solution of 3-acetylmercapto-6-methyl-4-[[[1-(S)-[(methylamino)carbonyl]-2-(4-methoxyphenyl)-ethyl]amino]carbonyl]heptanoic acid, methyl ester (E1; 100 mg, 0.21 mmol) in nitrogen-purged methanol (10 ml) was treated with 35% aqueous ammonia (0.5 ml), and the reaction mixture was stirred under nitrogen for 20 h. The solution was evaporated in vacuo, then was triturated with water, filtered and dried to give the title compound (46 mg, 52%), m.p. 80°-86° C. Observed mass 424.2028; $C_{21}H_{32}O_5N_2S$ requires 424.2033.

Each of the separated diastereoisomers of the S-acetyl compound of Example 1 (5-15 mg) were individually dissolved in nitrogen-purged methanol (1 ml) and treated with 35% aqueous ammonia (0.1 ml). The solutions were stirred at room temperature under nitrogen for 2 h, then were evaporated in vacuo, and the residues were triturated with water and dried to give:

Isomer A, m.p. 193°-196° C.:

δ (CDCl$_3$): 0.87 (6H, d, J=6Hz), 1.2-1.7 (3H, m), 1.67 (1H, d, J=9Hz), 2.32 (1H, dd, J=10, 15Hz), 2.41 (1H, m), 2.59 (1H, dd, J=4, 15Hz), 2.73 (3H, d, J=5Hz), 3.0 (2H, d, J=8Hz), 3.21 (1H, m), 3.70 (3H, s), 3.78 (3H, s), 4.59 (1H, q, J=7Hz), 5.66 (1H, brd), 6.34 (1H, d, J=8Hz), 6.83 (2H, d, J=9Hz) and 7.13 (2H, d, J=9Hz).

Observed mass. 424.2039; $C_{21}H_{32}N_2O_5S$ requires 424.2031. and

Isomer B:

δ (CDCl$_3$): 0.86 (6H, t, J=7Hz), 1.2-1.7 (3H, m), 2.00 (1H, d, J=9Hz), 2.49 (1H, m), 2.51 (1H, dd, J=9, 15Hz), 2.68 (1H, dd, J=5, 16 Hz), 2.73 (3H, d, J=5Hz), 2.97 (1H, dd, J=7, 13Hz), 3.07 (1H, dd, J=7H, 13Hz), 3.28 (1H, m), 3.72 (3H, s), 3.79 (3H, s), 4.55 (1H, q, J=7Hz), 5.64 (1H, brs), 6.33 (1H, d, J=7Hz), 6.84 (2H, d, J=8Hz) and 7.14 (2H, d, J=7Hz).

Observed mass. 424.2024; $C_{21}H_{32}N_2O_5S$ requires 424.2031.

EXAMPLE 3

3-Acetylmercapto-6-methyl-4-[[[1-(S)-[(methylamino)carbonyl]-2-(4-methoxyphenyl)ethyl]amino]carbonyl]-heptanoic acid, benzyl ester (E3)

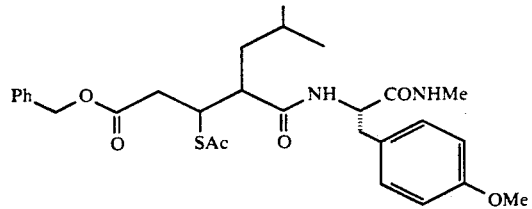

(E3)

The benzyl ester (D8) (41 g, 0.088 mole) was dissolved in thiolacetic acid (170 ml) and left to stand at room temperature under nitrogen for 19 days. Volatile material was removed in vacuo and the residue chromatographed on silica gel with initially ether, rising slowly to ethyl acetate. After removal of high R$_f$ impurities the title compound was obtained as a mixture of diastereomers as a pale yellow foam (29.76 g, 62.4%). (Found: C, 64.29; H, 7.16; N, 4.86. $C_{29}H_{38}N_2SO_6$ requires C, 64.18; H, 7.06; N, 5.16%). Later fractions contained olefinic material (D8). However, more complete reaction can be obtained by addition of a suitable base, for example triethylamine. An aliquot (2 ml) was removed from the above reaction mixture after 14 days, treated with triethylamine (3 drops) and left to stand for a further 5 days at room temperature under nitrogen. The same work-up procedure as for the bulk of the reaction mixture described above gave only the diastereomer mixture (E3) with no olefinic material remaining. 3-Mercapto-6-methyl-4-[[[1-(S)-[(methylamino)carbonyl]-2-(4-methoxyphenyl)ethyl]amino]carbonyl]heptanoic acid, benzyl ester (E4, Isomer A, 2.0 g 0.004 mol) was dissolved in chloroform (100 ml) under an atmosphere of nitrogen. The reaction mixture was cooled to 0° C. and acetic anhydride (2.04 g, 0.02 mol) was added followed by N-methylmorpholine (2.02 g, 0.02 mol). The reaction mixture was allowed to warm to room temperature, then stirred under nitrogen for 3 days.

The chloroform solution was washed with 10% aqueous citric acid solution then water, then dried (MgSO$_4$) and concentrated in vacuo to give a white solid which was recrystallised from ether to give the title compound as a single isomer (Isomer A) (1.4 g), m.p. 89°-90° C.

(Found: C,63.94; H,7.25; N,5.13. $C_{29}H_{38}N_2O_6S$ requires C,64.18; H,7.06; N,5.16%, δ (CDCl$_3$): 0.84(6H,t,J=7Hz), 1.17-1.71(3H,m), 2.27(3H, s), 2.45-2.7(3H,m), 2.7(3H,d,J=5Hz), 2.85-3.04(2H,m), 3.78(3H,s), 3.92(1H,m), 4.52(1H,q,J=8Hz), 5.12(2H,s), 5.52(1H,brd), 6.32(1H,d,J=8Hz), 6.79(2H,d,J=9Hz), 7.12(2H,d,J=9Hz) and 7.36(5H,m).

EXAMPLE 4

3-Mercapto-6-methyl-4-[[[1-(S)-[(methylamino)carbonyl]2-(4-methoxyphenyl)ethyl]amino]carbonyl]heptanoic acid, benzyl ester (E4)

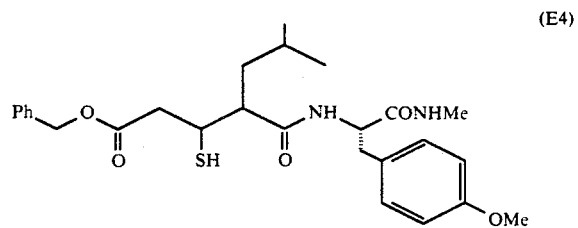

(E4)

An ice-cooled solution of 3-acetylmercapto-6-methyl-4-[[[1-(S)-[(methylamino)carbonyl]-2-(4-methoxyphenyl) ethyl]-amino]carbonyl]heptanoic acid, benzyl ester (E3; 1 g, 2 mmol) in nitrogen-purged methanol (100 ml) was treated with 35% aqueous ammonia (10 ml). The mixture was stirred at room temperature under nitrogen for 3 h and the precipitated solid (100 mg) was filtered off. The filtrate was evaporated in vacuo, and the residue was crystallised from methanol (5 ml) and ether (120 ml), to give a single isomer (isomer A) of the title compound (300 mg), m.p. 199°-201° C.

(Found: C,64.77; H,7.31; N,5.68. $C_{27}H_{36}N_2O_5S$ requires C,64.77; H,7.25; N,5.60%).

δ (CDCl$_3$): 0.84 (3H, d, J=7Hz), 0.86 (3H, d, J=7Hz), 1.3-1.7 (3H,m), 1.66 (1H, d, J=9Hz), 2.38 (1H, dd, J=9, 15Hz), 2.41 (1H, m), 2.66 (1H, dd, J=4, 15Hz), 2.73 (3H, d, J=5Hz), 2.97 (2H, d, J=8Hz), 3.22 (1H, m), 3.74 (3H, s), 4.57 (1H, q, J=8Hz), 5.14 (2H, s), 5.63 (1H, brd), 6.33 (1H, d, J=8Hz), 6.81 (2H, d, J=9Hz), 7.12 (2H, d, J=9Hz) and 7.36 (5H, m).

Column chromatography of the mother liquors on silica, eluting with 3:1 ether:chloroform gave two further single diastereoisomers.

Isomer B, the slower running isomer was obtained as a foam, which solidified on standing, mp 133°-135° C.

(Found: C,64.66; H,7.41; N,5.58. $C_{27}H_{36}N_2O_5S$ requires C,64.77; H,7.25; N,5.60%).

δ (CDCl$_3$): 0.73 (3H, d, J=7Hz), 0.79 (3H, d, J=7Hz), 1.2-1.7 (3H, m), 1.90 (1H, d, J=9Hz), 2.36 (1H, m), 2.64 (1H, dd, J=9, 17Hz), 2.69 (3H, d, J=6Hz), 2.81 (1H, dd, J=4, 17Hz), 2.94 (1H, dd, J=7,

16Hz), 3.03 (1H, dd, J=7, 16Hz), 3.26 (1H, m), 3.78 (3H, s), 4.59 (1H, q, J=7Hz), 5.15 (2H, m), 5.98 (1H, brd), 6.16 (1H, d, J=8Hz), 6.82 (2H, d, J=9Hz), 7.10 (2H, d, J=9Hz) and 7.36 (5H, m).

Isomer C, the faster running isomer was obtained as a gum.

δ (CDCl$_3$): 0.81 (3H, d, J=6Hz), 0.83 (3H, d, J=6Hz), 1.2–1.7 (3H, m), 1.99 (1H, d, J=9Hz), 2.47 (1H, m), 2.56 (1H, dd, J=8, 15Hz), 2.72 (1H, m), 2.72 (3H, d, J=6Hz), 2.96 (1H, dd, J=7, 15Hz), 3.04 (1H, dd, J=7, 15Hz), 3.29 (1H, m), 3.77 (3H, s), 4.55 (1H, q, J=7Hz), 5.16 (2H, s), 5.75 (1H, brd), 6.38 (1H, d, J=8Hz), 6.81 (2H, d, J=9Hz), 7.12 (2H, d, J=9Hz) and 7.36 (5H, m).

Isomer D was obtained from a mixture of isomers B and D by preparative HPLC (Lichrosorb diol), eluting with 18/82 (1% methanol/dichloromethane)/hexane.

δ (CDCl$_3$): 0.68 (3H, dd, J=7Hz), 0.78 (3H, d, J=7Hz), 1.1–1.6 (3H, m), 2.09 (1H, d, J=10 Hz), 2.36 (1H, m), 2.63 (1H, dd, J=6,17Hz), 2.74 (3H, d, J=6Hz), 2.85 (1H, dd, J=5,17Hz), 2.99 (1H, dd, J=7,16Hz), 3.09 (1H, dd, J=7,16Hz), 3.29 (1H, m), 3.79 (3H, s), 4.68 (1H, q, J=7Hz), 5.91 (1H, d, J=8Hz), 6.24 (1H, brd), 6.82 (2H, d, J=9Hz) and 7.10 (2H, d, J=9Hz).

EXAMPLE 5

3-Acetylmercapto-6-methyl-4-[[[1-(S)-[(methylamino)-carbonyl]-2-(4-methoxyphenyl)ethyl]amino]carbonyl]-heptanoic acid (E5)

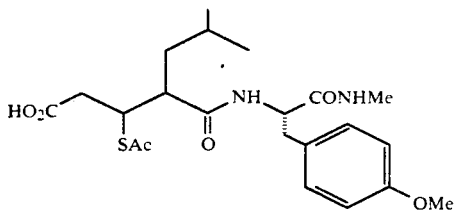

A solution of 3-acetylmercapto-6-methyl-4-[[[1-(S)-[(methylamino)carbonyl]-2-(4-methoxyphenyl)ethyl]amino]carbonyl]heptanoic acid, benzyl ester (E3; 300 mg. 0.55 mmol) in 4.5% formic acid/methanol (6 ml) was added, under nitrogen, to a stirred suspension of palladium black (310 mg) in the same solvent (15 ml). After 90 min the mixture was filtered through kieselguhr and evaporated in vacuo. Column chromatography using reverse phase silica (30 g) and eluting with 25% aqueous methanol gave two single diastereoisomers of the title compound, as monohydrates.

Isomer A, m.p. 92°–95° C. (54 mg).

(Found: C, 56.34; H, 7.11; N, 6.08. C$_{22}$H$_{32}$N$_2$O$_6$S.H$_2$O requires C, 56.15; H, 7.28; N, 5.95%).

δ (CDCl$_3$): 0.85 (3H, d, J=6Hz), 0.91 (3H, d, J=6Hz), 1.2–1.7 (3H, m), 2.31 (3H, s), 2.50 (1H, dd, J=3, 17Hz), 2.67 (1H, dd, J=7, 17Hz), 2.68 (3H, d, J=5Hz), 2.85–3.0 (2H, m), 3.15 (1H, t, J=10Hz), 3.74 (3H, s), 3.80 (1H, m), 4.80 (1H, q, J=8Hz), 6.36 (1H, m), 6.77 (2H, d, J=9Hz), 7.07 (2H, d, J=9Hz) and 8.41 (1H, d, J=10Hz. and Isomer B, m.p. 106°–110° C. (70 mg).

(Found: C, 56.33; H, 7.17; N, 6.15. C$_{22}$H$_{32}$N$_2$O$_6$S.H$_2$O requires C, 56.15; H, 7.28; N, 5.95%).

δ (CDCl$_3$): 0.77 (3H, s), 0.86 (3H, s), 1.1–1.7 (3H, m), 2.34 (3H, s), 2.73 (2H, d, J=4Hz), 2.82 (3H, d, J=4Hz), 2.8–3.0 (3H, m), 3.75 (3H, s), 3.88 (1H, brd, J=1Hz), 4.80 (1H, q, J=8Hz), 6.61 (1H, m), 6.78 (2H, d, J=9Hz), 7.11 (2H, d, J=9Hz) and 8.53 (1H, d, J=9Hz).

Similar treatment of the single isomer of the acetylmercapto compound (E3, Isomer A; 1.4 g, 2.6 mmol) gave the title compound as a single isomer (Isomer A), 980 mg (84%).

EXAMPLE 6

3-Mercapto-6-methyl-4-[[[1-(S)-[(methylamino)car-bonyl]2-(4-methoxyphenyl)ethyl]amino]carbonyl]hep-tanoic acid (E6)

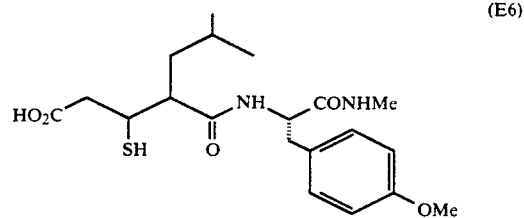

Each of the separate isomers of the S-acetyl compound of Example 5 (27–42 mg) were individually dissolved in nitrogen-purged methanol (4 ml) and treated with 35% aqueous ammonia (0.4 ml). The solutions were stirred at room temperature under nitrogen for 6 h, then were evaporated in vacuo, and the residues were triturated with ether to give:

Isomer A, m.p. 171°–176° C.:

δ (CDCl$_3$) 0.86 (6H, t, J=6Hz), 1.3–1.7 (3H, m), 1.79 (1H, d, J=9Hz), 2.43 (1H, dd, J=5, 15Hz), 2.66 (1H, dd, J=4, 15Hz), 2.72 (3H, d, J=5Hz), 2.8–3.1 (4H, m), 3.74 (3H, s), 4.73 (1H, q, J=7Hz), 6.29 (1H, brs), 6.89 (2H, d, J=9Hz), 7.09 (2H, d, J=9Hz) and 8.02 (1H, brd, J=9Hz), and Isomer B, m.p. 107°–110° C.:

δ (CDCl$_3$): 0.76 (3H, d, J=7Hz), 0.79 (3H, d, J=7Hz, 2.34 (1H, d, J=10Hz), 2.73 (2H, d, J=6Hz), 2.80 (3H, d, J=6Hz), 2.85–3.2 (4H, m), 3.77 (3H, s), 4.71 (1H, q, J=8Hz), 6.26 (1H, brs), 6.79 (2H, d, J=9Hz), 7.09 (2H, d, J=9Hz) and 7.94 (1H, brd, J=9Hz).

EXAMPLE 7

3-Benzoylmercapto-N$^5$-methyl-N$^1$-[1-(S)-[(methylamino)carbonyl]-2-(4-methoxyphenyl)ethyl]-2-(2-methylpropyl)pentanediamide (E7)

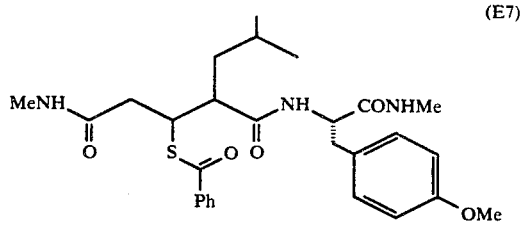

2-(1-Benzoylmercapto-2-[methylaminocarbonyl]ethyl)-4-methylpentanoic acid, tert-butyl ester (D11; 0.5 g) was treated with trifluoroacetic acid (10 ml) at 0° C. for 2 h and evaporated to dryness in vacuo to give 2-(1-benzoylmercapto-2-[methylaminocarbonyl]ethyl)-4-methylpentanoic acid.

[δ (CDCl$_3$) no signal at 1.5 ppm indicating absence of a tert-butyl group]

N,N-Dicyclohexylcarbodiimide (235 mg) and hydroxybenzotriazole (145 mg) was added to an ice-cooled solution of the above acid and O-methyl-L-tyrosine-N-methylamide (220 mg) in dry dichloromethane (20 ml), and the mixture was stirred at room temperature for 18 h. The precipitated solid was filtered off, and washed with a little dichloromethane, then the organic solution was washed successively with 1 N hydrochloric acid, 1 N sodium bicarbonate and water. The solution was dried (MgSO4) and evaporated to dryness in vacuo. The residual solid was chromatographed on neutral alumina using chloroform-pentane (1:1) as eluant. The solid product was triturated with ether to give the title compound (130 mg), m.p. 140°-144° C. as a mixture of diastereoisomers.

Observed M+ 527.2449. $C_{28}H_{37}N_3O_5S$ requires M 527.2453.

EXAMPLE 8

3-Mercapto-$N^5$-methyl-$N^1$-[1-(S)-[(methylamino)carbonyl]2-(4-methoxyphenyl)ethyl]-2-(2-methylpropyl)-pentanediamide (E8)

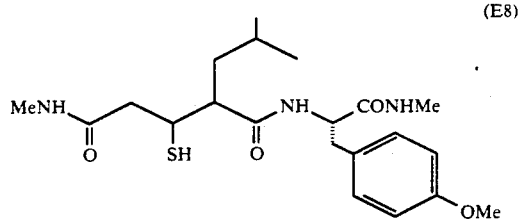

(E8)

An ice-cooled solution of 3-benzoylmercapto-$N^5$-methyl-$N^1$-[1-(S)-[(methylamino)carbonyl]-2-(4-methoxyphenyl)ethyl-2-(2-methylpropyl)pentanediamide (E7; 40 mg) in nitrogen-purged methanol (5 ml) was treated with 35% aqueous ammonia (2.5 ml) and the reaction mixture was stirred under nitrogen for 2 h. The solution was filtered and the filtrate was evaporated to dryness in vacuo. The residue was triturated with ether, filtered, and dried to give the title compound (20 mg, 62%), m.p. 175°-190° C. as a mixture of diastereoisomers. Observed M+ 423.2190. $C_{21}H_{33}N_3O_4S$ requires M 423.2191.

Similar treatment of 3-acetylmercapto-$N^5$-methyl-$N^1$-(1-(S)-[(methylamino)carbonyl]-2-(4-methoxyphenyl)-ethyl-2-(2-methylpropyl)pentanediamide (E11, Isomer A; 48 mg, 0.1 mmol) gave the title compound as a single isomer (Isomer A), (28 mg, 64%), mp 243°-250° C.

(Found: C,59.89; H,7.86; N,9.55. $C_{21}H_{33}N_3O_4S$ requires C,59.55; H,7.85; N,9.92%).

δ (CDCl3+drop d6-DMSO): 0.83(3H,d,J=8Hz), 0.85(3H,d, J=8Hz), 1.2–1.6(3H,m), 1.74(1H,d,J=7Hz), 2.0(1H,dd, J=11,13Hz), 2.10(1H,dd,J=3,13Hz), 2.65(6H,d,J=5Hz), 2.79(1H,dd,J=9,13Hz), 2.98(1H,dd,J=5,13Hz), 3.73(3H,s), 4.56(1H,m), 6.87(2H,d,J=9Hz), 7.15(2H,d,J=9Hz), 7.55 (2H,m) and 7.98(1H,d,J=9Hz).

EXAMPLE 9

3-Acetylmercapto-6-methyl-4-[[[1-(S)-[(methylamino)-carbonyl]-2-phenylethyl]amino]carbonyl]-heptanoic acid, methyl ester (E9)

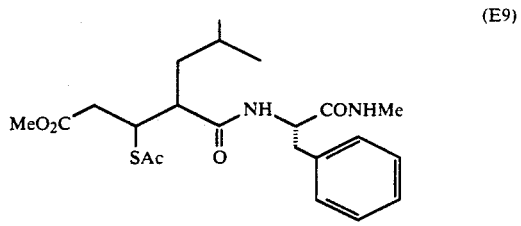

(E9)

A solution of 6-methyl-4-[[[1-(S)-[(methylamino)-carbonyl]-2-phenylethyl]amino]carbonyl]-hept-3-enoic acid, methyl ester (D12; 2.3 g, 6.3 mmol) in thiolacetic acid (20 ml) was stirred at room temperature for 14 days, then was evaporated to dryness in vacuo. The product was chromatographed on silica gel (100 g) eluting with 10 to 25% ethyl acetate/pentane, to give the title compound (1.35 g, 49%) (mixture of diastereoisomers).

The product was recrystallised (×2) from ethyl acetate to give a solid (0.7 g) m.p. 188°-189° C. which was shown by NMR to be a mixture of two diastereoisomers (ratio 3:1).

(Found C, 60.9; H, 7.3; N, 6.35. $C_{22}H_{32}N_2O_5S$ requires C, 60.55; H, 7.45; N, 6.4%).

δ (CDCl3): 0.85 (6H, m), 1.2–1.7 (3H, m), 2.3 (s) and 2.32 (s) (total 3H), 2.4 (1H, m), 2.6 (2H, m), 2.71 (3H, d, J=6Hz), 3.07 (2H, m), 3.66 (s) and 3.68 (s) (ratio 3:1 - total 3H), 3.9 (1H, m), 4.65 (1H, m), 5.78 (brd) and 5.83 (brd) (ratio 3:1 - total 1H), 6.43 (d, J=8Hz) and 6.51 (d, J=8Hz) (ratio 3:1 - total 1H) and 7.25 (5H, m).

EXAMPLE 10

3-Mercapto-6-methyl-4-[[[1-(S)-[(methylamino)carbonyl]-2-phenylethyl]amino]carbonyl]heptanoic acid, methyl ester (E10)

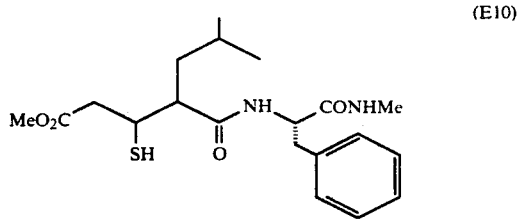

(E10)

An ice-cooled solution of 3-acetylmercapto-6-methyl-4-[[[1-(S)-[(methylamino)carbonyl]-2-phenylethyl]amino]carbonyl]heptanoic acid, methyl ester, m.p. 188°-189° C., (E9; 100 mg) in nitrogen-purged methanol (5 ml) was treated with 35% aqueous ammonia (2 ml) and the reaction mixture was stirred under nitrogen for 3.5 h. The solution was filtered, and the filtrate was evaporated to dryness in vacuo. The residue was triturated with water and the solid was collected and recrystallised from ethyl acetate-ether to give the title compound (25 mg), m.p. 169°-171° C., as a single diastereoisomer (Isomer A).

(Found: C, 60.65; H, 7.85; N, 7.05. $C_{20}H_{30}N_2O_4S$ requires C, 60.9; H, 7.65; N, 7.1%).

δ (CDCl₃): 0.85 (6H, d, J=5Hz), 1.2-1.7 (3H, m), 1.64 (1H, d, J=9Hz), 2.3 (1H, dd, J=9, 16Hz), 2.42 (1H, m), 2.58 (1H, dd, J=4, 16Hz), 3.07 (1H, d, J=8Hz), 3.2 (1H, m), 3.68 (3H, s), 4.65 (1H, q, J=8Hz), 5.75 (1H, brd), 6.39 (1H, d, J=8Hz) and 7.25 (5H, m).

EXAMPLE 11

3-Acetylmercapto-N⁵-methyl-N¹-[1-(S)-[(methylamino)carbonyl]-2-(4-methoxyphenyl)ethyl]-2-(2-methylpropyl)pentanediamide (E11)

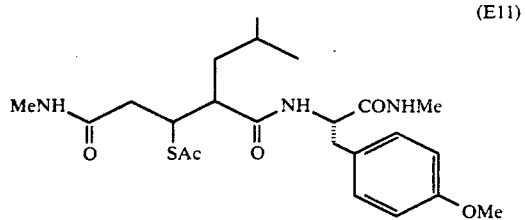

(E11)

Diisopropylethylamine (0.13 ml, 0.7 mmol) and ethyl chloroformate (0.07 ml, 0.7 mmol) were added to a solution of 3-acetylmercapto-6-methyl-4-[[[1-(S)-[(methylamino)carbonyl]-2-(4-methoxyphenyl)ethyl]amino]carbonyl]heptanoic acid (E5, Isomer A; 300 mg, 0.66 mmol) in dry THF (10 ml), at −20° C. After 15 min a solution of methylamine ( 20 mg) in THF (0.8 ml) was added dropwise and the mixture was stirred in an ice bath for 3 h. The solvent was evaporated in vacuo, and a solution of the residue in dichloromethane was washed successively with water, 1 M hydrochloric acid, water, saturated sodium hydrogen carbonate and brine. The solution was dried (MgSO₄) and evaporated in vacuo. Column chromatography on silica (10 g), eluting with 5% methanol/ethyl acetate gave the title compound, mp 195°-199° C.

(Found: C,58.97; H,7.78; N,.8.92. C₂₃H₃₅N₃O₅S requires C,59.33; H,7.58; N,9.03%).

δ (CDCl₃), 0.84(6H,q,J=3Hz), 1.2-1.7(3H,m), 2.10(1H,dd, J=7,15Hz), 2.30(3H,s), 2.31(1H,dd,J=5,15Hz), 2.68(1H, m), 2.74(3H,d,J=5Hz), 2.76(3H,d,J=5Hz), 2.95(1H,dd,J=6,14Hz), 3.08(1H,dd,J=6,14Hz), 3.78(3H,s), 3.83(1H,m), 4.63(1H,q,J=7Hz), 5.49(1H,brs), 5.88(1H,brs), 6.68(1H, J=7Hz), 6.82(2H,d,J=8Hz) and 7.14(2H,d,J=8Hz).

EXAMPLE 12

2-[3-Acetylmercapto-6-methyl-4-[[[1-(S)-[(methylamino)carbonyl]-2-(4-methoxyphenyl)ethyl]amino]carbonyl]heptanoylamino]ethanoic acid, t-butyl ester (E12)

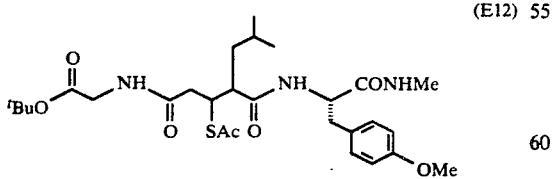

(E12)

A solution of 3-acetylmercapto-6-methyl-4-[[[1-(S)-[(methylamino)carbonyl]-2-(4-methoxyphenyl)ethyl]amino]carbonyl]heptanoic acid (E5, Isomer A; 90 mg, 0.2 mmol), N-ethyl-N'-dimethylaminopropylcarbodiimide hydrochloride (42 mg, 0.22 mmol), 1-hydroxybenzotriazole (34 mg, 0.22 mmol), t-butylglycine hydrochloride (37 mg, 0.22 mmol) and diisopropylethylamine (0.07 ml, 0.4 mmol) in dichloromethane (2 ml), was stirred at room temperature for 18 h. The mixture was diluted with dichloromethane and was washed successively with saturated sodium hydrogen carbonate, water, 1 M citric acid and brine. The solution was dried (NaSO₄) and evaporated in vacuo to leave the title compound as a single isomer (Isomer A) (74 mg, 68%), mp 192°-194° C. (ethyl acetate).

(Found: C,59.51; H,7.70; N,7.33. C₂₈H₄₃N₃O₇S requires C,59.45; H,7.66; N,7.43%).

δ (CDCl₃): 0.77(3H,d,J=6Hz), 0.83(3H,d,J=6Hz), 1.2-1.7 (3H,m), 1.47(9H,s), 2.30(3H,s), 2.35(2H,m), 2.56(1H, m), 2.77(3H,d,J=5Hz), 3.00(1H,dd,J=10,15Hz), 3.10(1H,dd,J=7,15Hz), 3.70(1H,dd,J=6,19Hz), 3.78(1H,s), 3.95(1H,dd,J=6,19Hz), 4.00(1H,m), 4.64(1H,q,J=7Hz), 6.05(1H,m), 6.33(1H,brt), 6.83(2H,d,J=9Hz), 7.14(2H,d,J=9Hz) and 7.43(1H,d,J=7Hz).

EXAMPLE 13

2-[3-Mercapto-6-methyl-4-[[[1-(S)-[(methylamino)carbonyl]-2-(4-methoxyphenyl)ethyl]amino]carbonyl]heptanoylamino]ethanoic acid, t-butyl ester (E13)

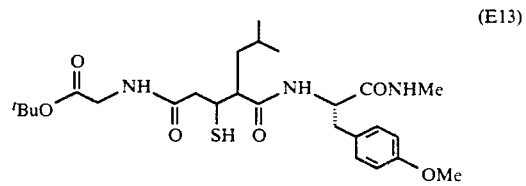

(E13)

An ice-cooled solution of 2-[3-acetylmercapto-6-methyl-4-[[[1-(S)-[(methylamino)carbonyl]-2-(4-methoxyphenyl) ethyl]amino]carbonyl]heptanoylamino]ethanoic acid, t-butyl ester (E12, Isomer A; 30 mg, 0.053 mmol) in nitrogen-purged methanol (4 ml) was treated with 35% aqueous ammonia (0.3 ml), under nitrogen, and was stirred for 2 h at room temperature. The solvents were evaporated in vacuo and the residue was triturated with hexane to give the title compound as a single isomer (Isomer A), mp 223°-226° C.

(Found: C,59.52; H,7.68; N,7.88. C₂₆H₄₁N₃O₆S requires C,59.63; H,7.89; N,8.02%).

δ (CDCl₃): 0.84(6H,dd,J=6,8Hz), 1.3-1.7(3H,m), 1.48 (9H,s), 2.24(1H,d,J=10Hz), 2.28(1H,m), 2.45(1H,dd,J=15, 5Hz), 2.50(1H,m), 2.76(3H,d,J=5Hz), 2.99(1H,dd,J=15, 9Hz), 3.09(1H,dd,J=15,7Hz), 3.12(1H,m), 3.77(3H,s), 3.89(1H,dd,J=5,7Hz), 4.64(1H,q,J=8Hz), 5.98(1H,brd), 6.47(1H,brt), 6.84(2H,d,J=9Hz), 7.15(2H,d,J=9Hz) and 7.18(1H,brs).

EXAMPLE 14

2-[3-Acetylmercapto-6-methyl-4-[[[1-(S)-[(methylamino)carbonyl]-2-(4-methoxyphenyl)ethyl]amino]carbonyl]heptanoylamino]ethanoic acid (E14)

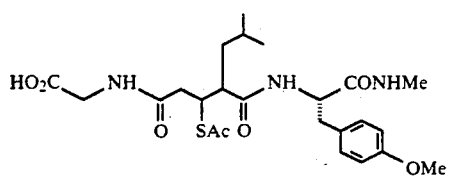
(E14)

A solution of 2-[3-acetylmercapto-6-methyl-4-[[[1-(S)-[(methylamino)carbonyl]-2-(4-methoxyphenyl)ethyl]amino]carbonyl]heptanoylamino]ethanoic acid, t-butyl ester (E12, Isomer A; 60 mg, 0.11 mmol) in trifluoroacetic acid (1.5 ml) and water (0.05 ml) was stirred in an ice bath for 1 h, then at room temperature for 2 h. The solvent was evaporated in vacuo and the residue was azeotroped dry with toluene to leave the title compound as a single isomer (Isomer A), mp 188°–192° C.

EXAMPLE 15

2-[3-Mercapto-6-methyl-4-[[[1-(S)-[(methylamino)carbonyl]-2-(4-methoxyphenyl)ethyl]amino]carbonyl]heptanoylamino]ethanoic acid (E15)

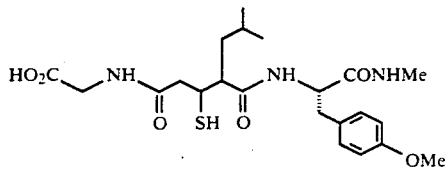
(E15)

A solution of 2-[3-acetylmercapto-6-methyl-4-[[[1-(S)-[(methylamino)carbonyl]-2-(4-methoxyphenyl)ethyl]amino]carbonyl]heptanoylamino]ethanoic acid (E14, Isomer A; 15 mg, 0.029 mmol) in nitrogen-purged methanol (5 ml) was cooled in ice and treated with 35% aqueous ammonia (0.3 ml). After 2 h the solvents were evaporated in vacuo and the residue was triturated with ethyl acetate to give the title compound as a single isomer (Isomer A), 11 mg (80%), mp 228°–231° C.

EXAMPLE 16

3-Acetylmercapto-$N^5$-(aminocarbonyl)methyl-$N^1$-[1-(S)-[(methylamino)carbonyl]-2-(4-methoxyphenyl)ethyl]-2-(2-methylpropyl)pentanediamide (E16)

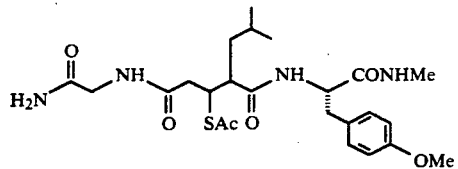
(E16)

A mixture of 3-acetylmercapto-6-methyl-4-[[[1-(S)-[(methylamino)carbonyl]-2-(4-methoxyphenyl)ethyl]amino]carbonyl]heptanoic acid (E5, Isomer A; 226 mg, 0.5 mmol), N-ethyl-$N^1$-dimethylaminopropylcarbodiimide hydrochloride (116 mg, 0.6 mmol), 1-hydroxybenzotriazole (90 mg, 0.58 mmol), glycinamide hydrochloride (64 mg, 0.58 mmol) and diisopropylethylamine (0.2 ml, 1.14 mmol) in dichloromethane was stirred at 5° C. for 2 h then at room temperature overnight. The mixture was cooled in ice and the solid was collected by filtration and washed well with dichloromethane. The solid was triturated with 1 M citric acid, then filtered, washed with water and dried. Recrystallisation from methanol/ether gave the title compound as a single isomer (Isomer A), 75 mg (30%) mp 218°–219° C.

δ (d$_6$-DMSO): 0.78(6H,t,J=7Hz), 1.1–1.5(3H,m), 2.1–2.3 (2H,m), 2.24(1H,s), 2.55(3H,d,J=5Hz), 2.74(1H,dd,J=10,14Hz), 2.85(1H,dd,J=5,14Hz), 3.56(2H,d,J=6Hz), 3.68(3H,s), 3.77(1H,m), 4.43(1H,m), 6.81(2H,d,J=9Hz), 7.10(2H,brd), 7.14(2H,d,J=9Hz), 7.79(1H,brq), 8.00(1H,t,J=6Hz) and 8.12(1H,d,J=8Hz).

EXAMPLE 17

$N^5$-(Aminocarbonyl)methyl-3-mercapto-$N^1$-[1-(S)-[(methyl amino)carbonyl]-2-(4-methoxyphenyl)ethyl]-2-(2-methylpropyl)pentanediamide (E17)

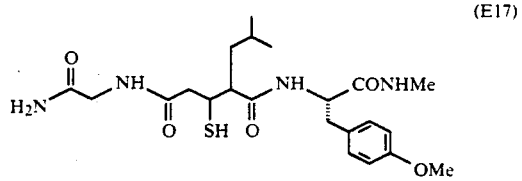
(E17)

An ice-cooled solution of 3-acetylmercapto-$N^5$-(aminocarbonyl)methyl-$N^1$-[1-(S)-[(methylamino)carbonyl]-2-(4-methoxyphenyl)ethyl]-2-(2-methylpropyl)-pentanediamide (E16, Isomer A; 44 mg, 0.087 mmol) in nitrogen-purged methanol (5 ml) was treated with 35% aqueous ammonia (0.4 ml) and was stirred at room temperature for 2.5 h. The solvent was evaporated in vacuo and the residue was triturated with ether to leave the title compound as a single isomer (Isomer A), 28 mg (70%), mp 247°–252° C.

δ (d$_6$-DMSO): 0.77(3H,d,J=6Hz), 0.82(3H,d,J=6Hz), 1.2–1.5(3H,m), 2.04(2H,m), 2.30(1H,d,J=7Hz), 2.33(1H,m), 2.57(3H,d,J=5Hz), 2.70(1H,d,J=10,14Hz), 2.86(1H,dd,J=5,14Hz), 3.08(1H,m), 3.62(2H,q,J=5Hz), 3.67(3H,s), 4.46(1H,m), 6.80(2H,d,J=9Hz), 7.10(2H,brd), 7.15(2H,d,J=9Hz)), 7.81(1H,m), 8.06(1H,t,J=5Hz) and 8.18(1H,d,J=8Hz).

EXAMPLE 18

1-[3-Acetylmercapto-6-methyl-4-[[[1-(S)-[(methylamino)carbonyl]-2-(4-methoxyphenyl)ethyl]amino]carbonyl]heptanoyl]-4-methylpiperazine (E18)

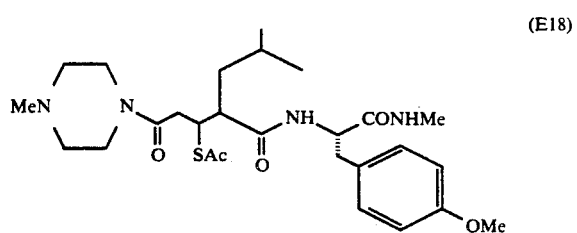
(E18)

A mixture of 3-acetylmercapto-6-methyl-4-[[[1-(S)-[(methylamino)carbonyl]-2-(4-methoxyphenyl)ethyl]amino]-carbonyl]heptanoic acid (E5, Isomer A; 226 mg, 0.5 mmol), $N,N^1$-dicyclohexylcarbodiimide (103 mg, 0.5 mmol), 1-hydroxybenzotriazole (76 mg, 0.5 mmol) and N-methylpiperazine (0.05 ml, 0.5 mmol) in dichloromethane (8 ml) was stirred at 5° C. for 1 h, then at room temperature overnight. After cooling, the precipitated solid was filtered off. The solution was diluted with dichloromethane and extracted with 0.25 M citric acid. The extracts were washed with dichloromethane then basified with 10% sodium carbonate, and extracted with ether. The ether extracts were washed with brine, dried ($Na_2SO_4$) and evaporated in vacuo. Trituration of the oily residue with ether, followed by recrystallisation of the resulting solid from ethyl acetate/hexane gave the title compound as a single isomer (Isomer A), 98 mg (37%) mp 133°-138° C. (Found: C,60.48; H,8.15; N,10.40. $C_{27}H_{42}N_4O_4S$ requires C,60.65; H,7.92; N,10.48%).

δ ($CDCl_3$): 0.85(6H,q,J=3Hz), 1.2-1.5(3H,m), 2.30(6H,s), 2.38(4H,brs), 2.33-2.8(3H,m), 2.70(3H,d,J=5Hz), 2.98 (2H,d,J=7Hz), 3.4(2H,brs), 3.5-3.7(2H,brm), 3.78(3H,s), 3.95(1H,q,J=6Hz), 4.54(1H,q,J=7Hz), 5.71(1H,brd), 6.64(1H,brd), 6.82(2H,d,J=9Hz) and 7.15(2H,d,J=9Hz).

EXAMPLE 19

1-[3-Mercapto-6-methyl-4-[[[1-(S)-[(methylamino)carbonyl]-2-(4-methoxyphenyl)ethyl]amino]carbonyl]heptanoyl]-4-methylpiperazine (E19)

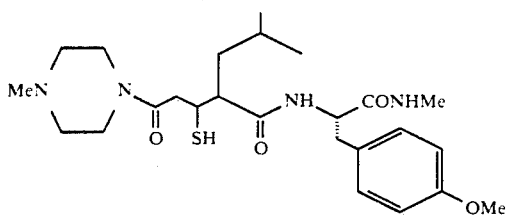

(E19)

A solution of 1-[3-acetylmercapto-6-methyl-4-[[[1-(S)-[(methylamino)carbonyl]-2-(4-methoxyphenyl)ethyl]amino]-carbonyl]heptanoyl]-4-methylpiperazine (E18, Isomer A; 60 mg, 0.112 mmol) in methanol (5 ml) was purged with nitrogen and cooled in ice, then was treated with 35% aqueous ammonia (0.4 ml). After 6 h at room temperature, the solvents were evaporated in vacuo and the residue was triturated with hexane to give the title compound as a single isomer (Isomer A), mp 65°-68° C.

δ ($CDCl_3$): 0.87(6H,d,J=6Hz), 1.3-1.7(3H,m), 1.85(1H,d,J=8Hz), 2.35(7H,m), 2.42(1H,dd,J=8,16Hz), 2.54(1H,m), 2.61(1H,dd,J=4,16Hz), 2.74(3H,d,J=5Hz), 3.01(2H,d,J=8Hz), 3.30(1H,m), 3.48(2H,brs), 3.65(2H,brm), 3.79(3H,s), 4.58(1H,q,J=8Hz), 5.35(1H,brm), 5.74(1H,brd), 6.52(1H,d,J=8Hz), 6.82(2H,d,J=9Hz) and 7.15(2H,d,J=9Hz).

EXAMPLE 20

1-[3-Acetylmercapto-6-methyl-4-[[[1-(S)-[(methylamino)carbonyl]-2-(4-methoxyphenyl)ethyl]amino]carbonyl]heptanoyl]morpholine hydrate (E20)

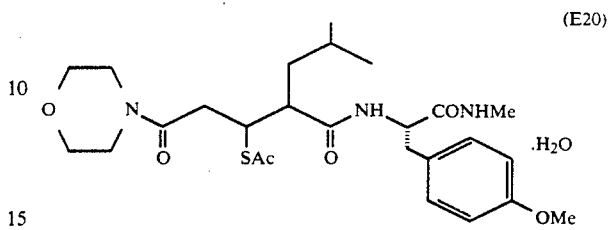

(E20)

To a solution of 3-acetylmercapto-6-methyl-4-[[[1-(S)-[(methylamino)carbonyl]-2-(4-methoxyphenyl)ethyl]-amino]carbonyl]heptanoic acid (E5, Isomer A; 290 mg, 0.64 mmol) in acetonitrile (10 ml) at 0° C. was added 1,1'-carbonyl diimidazole (104 mg, 0.64 mmol) and the solution was stirred under nitrogen at 0° C. for 1 h. A solution of morpholine ((56 mg, 0.64 mmol) in acetonitrile (2 ml) was then added dropwise, and the solution was left at room temperature overnight. The mixture was evaporated to dryness in vacuo and then dissolved in a mixture of ethyl acetate and chloroform (4:1; 30 ml) and washed successively with sodium carbonate, 1 M-hydrochloric acid and water. The organic fraction was dried ($MgSO_4$) and chromatographed on silica gel 60 (100 g). Elution with 5% methanol-ethyl acetate gave the title compound (70 mg) as a single isomer (Isomer A), m.p. 146°-149° C., after trituration with ether.

(Found: C,57.73; H,7.64; N,7.59. $C_{26}H_{39}N_3O_6S.H_2O$ requires C,57.86; H,7.66; N,7.79%).

δ ($CDCl_3$): 0.86(d,J=Hz) and 0.87(d,J=5Hz) (total 6H), 1.2-1.7(2H,m), 2.32(3H,s), 2.48(1H,dd,J=4,16Hz), 2.62(1H,dd,J=4,16Hz), 2.72(4H,brd,J=5Hz), 2.98(2H,d,J=7Hz), 3.3-3.75(8H,m), 3.76(3H,s), 3.96(1H,q,J=6Hz), 4.54(1H,q,J=6Hz), 5.69(1H,brd), 6.61(1H,d,J=7Hz), 6.84(2H,d,J=8Hz) and 7.16(2H,d,J=8Hz).

EXAMPLE 21

1-[3-Mercapto-6-methyl-4-[[[1-(S)-[(methylamino)carbonyl]-2-(4-methoxyphenyl)ethyl]amino]carbonyl]heptanoyl]morpholine hemihydrate (E21)

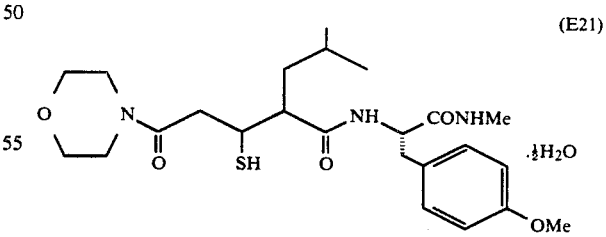

(E21)

A solution of 1-[3-acetylmercapto-6-methyl-4-[[[1-(S)-[(methylamino)-carbonyl]-2-(4-methoxyphenyl)ethyl]amino]carbonyl]heptanoyl]morpholine (E20, Isomer A; 12 mg) in methanol (3 ml) was purged with nitrogen and cooled in ice. The solution was treated with 35% aqueous ammonia (1.5 ml) at 0° C. for 0.5 h and then allowed to warm up to room temperature. After 1.5 h at room temperature the solution was evaporated to dryness in vacuo and the residue was washed twice with ether to give the title compound as a single isomer (Isomer A) m.p. 106°-108° C.

(Found: C,58.81; H,7.92; N,8.75. $C_{24}H_{37}N_3O_5S$ 0.5$H_2O$ requires C,58.99; H,7.83; N,8.60%).

δ (CDCl$_3$): 0.87(6H,d,J=7Hz), 1.35-1.5(2H,m), 1.84(1H,d,J=9Hz), 2.40(1H,dd,J=8Hz), 2.54(1H,m), 2.57(1H,dd,J=4,16Hz), 2.72(3H,d,J=6Hz), 3.01((2H,d,J=7Hz), 3.32(1H,m), 3.35-3.75(8H,m), 3.78(3H,s), 4.58(1H,q,J=8Hz), 5.77(1H,bd), 6.58(1H,d,J=8Hz), 6.82(2H,d,J=8Hz) and 7.15(2H,d,J=8Hz).

EXAMPLE 22

3-Acetylmercapto-6-methyl-4-[[[1-(S)-[(methylamino)-carbonyl]-2-(4-methoxyphenyl)ethyl]amino]carbonyl]-heptanoic acid, tert-butyl ester (E22)

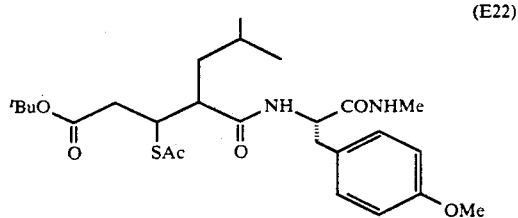

(E22)

A solution of 6-methyl-4-[[[1-(S)-[(methylamino)-carbonyl]-2-(4-methoxyphenyl)ethyl]amino]carbonyl]-hept-2(and 3)-enoic acid, tert-butyl ester (D14; 3 g) in thiolacetic acid (15 ml) was left at room temperature for 14 days, then evaporated to dryness in vacuo. Column chromatography on silica gel, eluting with ethyl acetate-pentane (1:1) gave the title compound (1.2 g) as a mixture of isomers.

A single diastereoisomer (Isomer A), m.p. 147°-151° C. (from ether-pentane), was obtained by preparative HPLC (Lichrosorb diol), eluting with 15/85 (1% methanol/dichloromethane)/hexane.

(Found: C,61.08; H,7.94; N,5.53. $C_{26}H_{44}ON_2O_6S$ requires C,61.39; H,7.93; N,5.51%).

δ (CDCl$_3$): 0.84(d,H=5Hz) and 0.86(d,J=5Hz) (total 6H), 1.2-1.7(2H,m), 1.44(9H,s), 2.30(3H,s), 2.49(1H,dd,J=7,17Hz), 2.58(1H,dd,J=5,17Hz), 2.60(1H,m), 2.70(3H,d,J=5Hz), 2.93(1H,dd,J=8,14Hz), 3.04(1H,dd,J=7,14Hz), 3.79(3H,s), 3.92(1H,q,J=6Hz), 4.52(1H,q,J=7Hz), 5.52(1H,brs), 6.37(1H,d,J=8Hz), 6.82(2H,d,J=8Hz) and 7.15(2H,d,J=8Hz).

EXAMPLE 23

3-Mercapto-6-methyl-4-[[[1-(S)-[(methylamino)carbonyl]2-(4-methoxyphenyl)ethyl]amino]carbonyl]heptanoic acid, tert-butyl ester (E23)

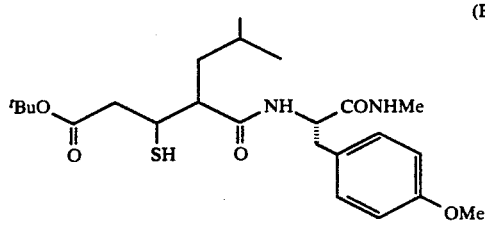

(E23)

An ice-cooled solution of 3-acetylmercapto-6-methyl-4-[[[1-(S)-[(methylamino)carbonyl]-2-(4-methoxyphenyl)-ethyl]amino]carbonyl]heptanoic acid, tert-butyl ester (E22) (23 mg) in nitrogen-purged methanol (3 ml) was treated with 35% aqueous ammonia (1.5 ml) and the reaction mixture was stirred under nitrogen for 3 h. The solution was filtered, and the filtrate was evaporated to dryness in vacuo. The residue was partitioned between chloroform (5 ml) and water (2 ml). The organic layer was dried (MgSO$_4$) and evaporated to dryness in vacuo. The product was recrystallised from ether-hexane to give the title compound, (Isomer A), m.p. 133°-137° C.

(Found C,61.72; H,8.45; N,5.90. $C_{24}H_{38}N_2O_5S$ requires C,61.77; H,8.21; N,6.00%).

δ (CDCl$_3$): 0.86(6H,d,J=5Hz), 1.3-1.75(2H,m), 1.46(9H,s), 1.65(1H,d,J=9Hz), 2.25(1H,dd,J=8,14Hz), 2.44(1H,m), 2.55(1H,dd,J=4,14Hz), 2.72(3H,d,J=5Hz), 3.02(2H,d,J=7Hz), 3.20(1H,m), 3.77(3H,s), 4.59(1H,q,J=7Hz), 5.77(1H,brd), 6.44(1H,d,J=8Hz), 6.82(2H,d,J=8Hz) and 7.15(2H,d,J=8Hz).

EXAMPLE 24

1-[3-Acetylmercapto-6-methyl-4-[[[2-(R)-benzyloxy-1-(S)-[(methylamino)carbonyl]propyl]amino]carbonyl]-heptanoic acid, methyl ester (E24)

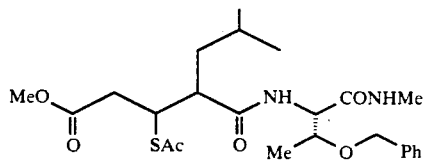

(E24)

A solution of 6-methyl-4-[[[2-(R)-benzyloxy-1-(S)-[(methylamino)carbonyl]propyl]amino]carbonyl]hept-2(and 3)-enoic acid, methyl esters (D15; 4.4 g) in thiolacetic acid (25 ml) was left at room temperature for 21 days, then was evaporated to dryness in vacuo and chromatographed on silica gel (150 g). Elution with ethyl acetate/pentane (1:1) gave the title compound as a 3:2 mixture of diastereoisomers (1.7 g)

(Isomers A/B), m.p. 105°-106° C. (from ether-pentane).

(Found: C,59.95; H,7.74; N,5.84. $C_{24}H_{36}N_2O_6S$ requires C,59.98; H,7.55; N,5.83%).

δ (CDCl$_3$): 0.90(m), 1.11(d,J=5Hz) and 1.15(d,J=5Hz) (ratio 3:2), 1.33(m), 1.53(m), 1.68(m) 2.32(s), 2.6-2.85(m), 3.66(s) and 3.67(s) (ratio 3:2), 4.08(m), 4.55(brs), 4.67(s), 6.45(brs), 6.75(d,J=6Hz), 6.84(d,J=6Hz) and 7.35(m). Further elution gave the title compound as a 2:1 mixture of diastereoisomers (2.1 g) (Isomers C/D), m.p. 111°-113° C. (from ether-pentane).

Found: C,60.35; H,7.25; N,5.84. $C_{24}H_{36}N_2O_6S$ requires C,59.98; H,7.55; N,5.83%).

δ (CDCl$_3$): 0.88(m), 1.13(t,J=5Hz), 1.32(m), 1.52(m), 1.62-1.80(m), 2.33(s), 2.6-2.82(m), 3.64(s), 3.66(s), 4.0-4.5(m), 4.19-4.24(m), 4.50(m), 4.58-4.64(m), 6.62(m), 6.79(m) and 7.3(m).

EXAMPLE 25

3-Mercapto-6-methyl-4-[[[2-(R)-benzyloxy-1-(S)-[(methylamino)carbonyl]propyl]amino]carbonyl]heptanoic acid, methyl ester (E23)

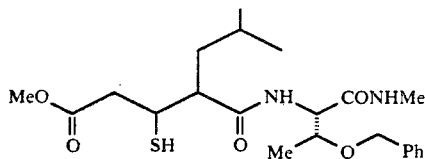

Each of the mixtures of diastereoisomers (A/B and C/D) of the S-acetyl compound of Example 24 were individually treated with 35% aqueous ammonia in the usual manner, to give the title compound;

Isomer (A/B) (3:2 ratio of diastereoisomers), m.p. 113°–119° C. (from $H_2O$).

(Found: C,59.04; H,7.88; N,6.26. $C_{22}H_{34}N_2O_5S$ $0.5H_2O$ requires C,57.87; H,7.95; N,6.13%).

δ (CDCl$_3$): 0.94(m), 1.12(d,J=5Hz), 1.13(d,J=5Hz), 1.38(m), 1.5(m), 1.71(mm), 1.90(0.6H,d,J=8Hz), 2.06(0.4H,d,J=8Hz), 2.57(m), 2.82(m), 3.37(m), 3.72(s), 4.14(m), 4.59(brs), 4.67(s), 6.5(m), 6.78(m) and 7.33(m).

Isomer (C/D) (2:1 ratio of diastereoisomers), m.p. 72°–76° C. (from ether). (Found: C,60.33; H,7.97; N,6.40. $C_{22}H_{34}N_2O_5S$ requires C,60.25; H,7.81; N,6.39%).

δ (CDCl$_3$): 0.95(m), 1.15(t,J=6Hz), 1.3(m), 1.41(m), 1.75(m), 2.01(0.66H,d,J=8Hz), 2.21(0.33H,d,J=8H), 2.54(m), 2.66(m), 2.82(m), 3.37(m), 3.72(s), 4.2(m), 4.38(m)), 4.6(m), 6.55(br.d,J=8Hz) 6.7(m), 6.9(br.s) and 7.35(m).

EXAMPLE 26

3-Acetylmercapto-6-methyl-4-[[[1-(S)-[(methylamino)carbonyl]-2-(3-indolyl)ethyl]amino]carbonyl]heptanoic acid, methyl ester (E26)

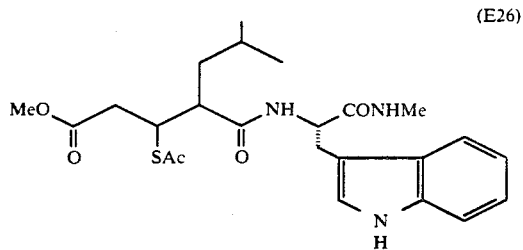

A solution of 6-methyl-4-[[[1-(S)-[(methylamino)-carbonyl]-2-(3-indolyl)ethyl]amino]carbonyl]hept-2(and 3)-enoic acid, methyl ester (D16; 2.5 g) in thiolacetic acid (100 ml) was left at room temperature for 28 days, then was evaporated to dryness in vacuo. Column chromatography (150 g) of the residue eluting initially with ether, and then ether-chloroform (1:1) gave the title compound (0.32 g) as a single isomer (Isomer A), m.p. 134°–136° C. (from ether).

(Found: C,60.32; H,6.88; N,8.80. $C_{24}H_{33}N_3O_5S$ requires C,60.61; H,6.99; N,8.83%).

δ (CDCl$_3$): 0.84(d,J=5Hz) and 0.85(d,J=5Hz) (total 6H), 1.2–1.75 (2H,m), 2.29(3H,s), 2.5–2.7(3H,m), 2.64(3H,d,J=5Hz), 3.11(1H,dd,J=8,14Hz), 3.3(1H,dd,J=6,14Hz), 3.62(3H,s), 3.94(1H,m), 4.72(1H,q,J=7Hz), 5.64(1H,brd), 6.52(1H,d,J=8Hz), 7.05–7.25(3H,m), 7.36(1H,d,J=7Hz), 7.72(1H,d,J=7Hz) and 8.17(1H,s).

EXAMPLE 27

3-Mercapto-6-methyl-4-[[[1-(S)-[(methylamino)carbonyl]2-(3-indolyl)ethyl]amino]carbonyl]heptanoic acid, methyl ester (E27)

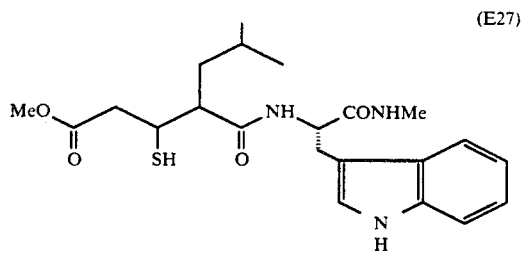

An ice-cooled solution of 3-acetylmercapto-6-methyl-4-[[[1-(S)-[(methylamino)carbonyl]-2-(3-indolyl)ethyl]-amino]carbonyl]heptanoic acid, methyl ester (E26; 0.1 g) in nitrogen-purged methanol (5 ml) was treated with 35% aqueous ammonia (1.5 ml). The mixture was stirred at room temperature under nitrogen for 2 h. The solution was evaporated to dryness in vacuo and the residue was triturated with cold ether to give the title compound as a single isomer (Isomer A), (52 mg), m.p. 73°–75° C.

(Found: C,60.69; H,7.35; N,9.64%. $C_{22}H_{31}N_3O_4S$ requires C,60.95; H,7.21; N,9.69%).

δ (CDCl$_3$) 0.87(6H,d,J=6Hz), 1.4–1.7(2H,m), 1.67(1H,d,J=9Hz), 2.37(1H,dd,J=5,15Hz), 2.41(1H,m), 2.60(1H,dd,J=3,15Hz), 2.65(3H,d,J=5Hz), 3.13(1H,dd,J=7,14Hz), 3.21(1H,m), 3.30(1H,dd,J=7,14Hz), 3.67(3H,s), 4.75(1H,q,J=7Hz), 5.68(1H,brd), 6.53(1H,d,J=8Hz), 7.05–7.25(3H,m), 7.35(1H,d,J=8Hz), 7.71(1H,d,J=8Hz) and 8.13(1H,s).

EXAMPLE 28

3-Acetylmercapto-N'-[1-(S)-[(methylamino)carbonyl]-2-(4-methoxyphenyl)ethyl]-2-(2-methylpropyl)pentanediamide (E28)

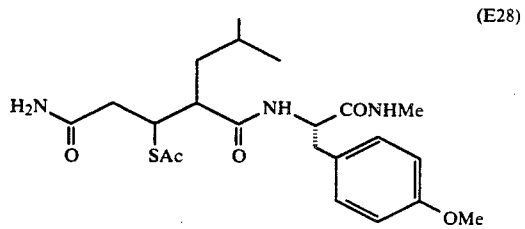

The title compound, m.p. 235°–240° C., was prepared from the compound of Example 5 and ammonia by an analogous procedure to that described in Example 11.

EXAMPLE 29

3-Mercapto-N'-[1-(S)-[(methylamino)carbonyl]-2-(4-methoxyphenyl)ethyl]-2-(2-methylpropyl)pentanediamide (E29)

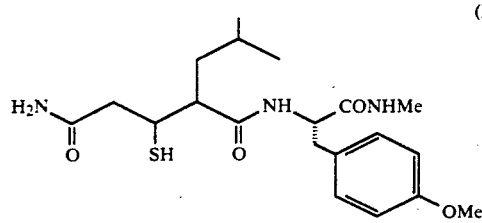

The title compound, m.p. 221°–225° C., was prepared from the compound of Example 28 by an analogous procedure to that described in Example 10.

EXAMPLE 30

3-Acetylmercapto-6-methyl-4-[[[1-(S)-[(methylamino)carbonyl]-2-(4-methoxyphenyl)ethyl]amino]carbonyl]-heptanoylglycine, ethyl ester (E30)

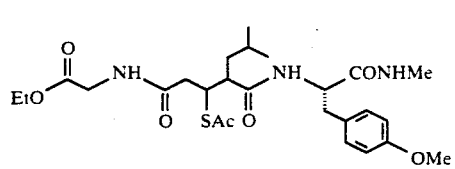

The title compound, m.p. 190°–198° C., was prepared from the compound of Example 5 and ethylglycine hydrochloride by an analogous procedure to that described in Example 12.

EXAMPLE 31

3-Mercapto-6-methyl-4-[[[1-(S)-[(methylamino)carbonyl]-2-(4-methoxyphenyl)ethyl]amino]carbonyl]heptanoylglycine, ethyl ester (E31)

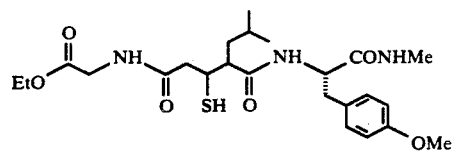

The title compound, m.p. 221°–228° C., was prepared from the compound of Example 30 by an analogous procedure to that described in Example 10.

EXAMPLE 32

3-Acetylmercapto-6-methyl-4-[[[1-(S)-(aminocarbonyl)-2-phenylethyl]amino]carbonyl]heptanoic acid, methyl ester (E32)

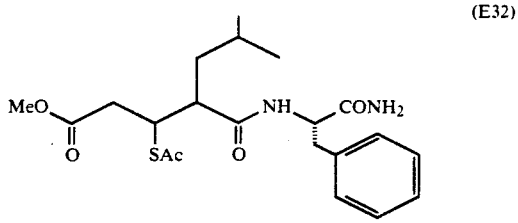

The title compound was prepared from 6-methyl-4-[[[1-(aminocarbonyl)-2-phenylethyl]amino)carbonyl]-hept-2(and 3)-enoic acid, methyl ester and thiolacetic acid by an analogous procedure to that described in Example 26. Silica gel chromatography gave mixtures of diastereoisomers (Isomer A/B), m.p. 160°–164° C. and (Isomer C/D), m.p. 50°–54° C. (after trituration with ether). The intermediate hept-2(and 3)-enoic acids were prepared from 4-methoxycarbonyl-2-(2-methylpropyl)but-2-enoic acid and L-phenylalanine as described in Description 12.

EXAMPLE 33

3-Mercapto-6-methyl-4-[[[1-(S)-(aminocarbonyl)-2-phenylethyl]amino]carbonyl]heptanoic acid, methyl ester (E33)

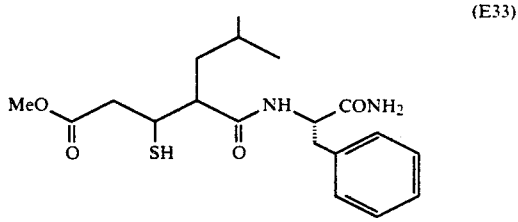

The title compound, isolated as a mixture of diastereoisomers, (Isomer A/B), and (Isomer C/D), m.p. 64°–66° C. was prepared from the compound of Example 32 by an analogous procedure to that described in Example 10. The crude product was purified by silica gel chromatography using ethyl acetate as the eluent.

EXAMPLE 34

3-Acetylmercapto-6-methyl-4-[[[1-(S)-[(methylamino)carbonyl]-2-(4-methoxyphenyl)ethyl]amino]carbonyl]-heptanoyl-D-leucine, t-butyl ester (E34)

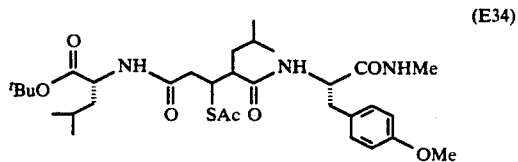

The title compound was prepared from the compound of Example 5 and t-butylleucine hydrochloride by an analogous procedure to that described in Example 12 and exhibited a m.p. of 148°–157° C.

EXAMPLE 35

3-Acetylmercapto-6-methyl-4-[[[1-(S)-[(Methylamino)-carbonyl]-2-(4-methoxyphenyl)ethyl]amino]carbonyl]-heptanoyl-D-leucine, (E35)

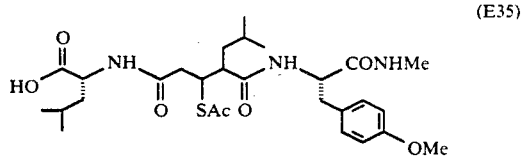

The title compound was prepared from the compound of Example 34 using an analogous procedure to that described in Example 14 and exhibited a m.p. of 195°–200° C.

EXAMPLE 36

3-Mercapto-6-methyl-4-[[[1-(S)-[(methylamino)carbonyl]-2-(4-methoxyphenyl)ethyl]amino]carbonyl]heptanoyl-D-leucine (E36)

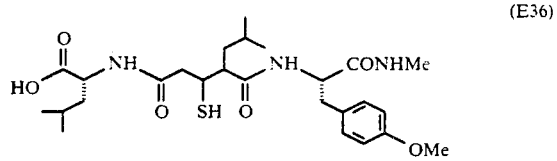

The title compound was prepared from the compound of Example 35 using an analogous procedure to that described in Example 15 and exhibited a m.p. of 216°–220° C.

EXAMPLE 37

N-[N-[3-Acetylmercapto-2-(2-methylpropyl)-1-oxo-4-[(phenylmethoxy)carbonyl]butyl]-L-leucyl-L-alanine, methyl ester. (E37)

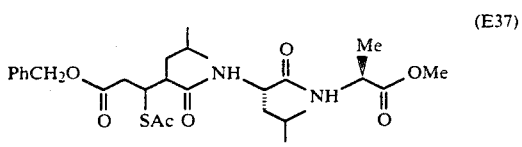

The title compound was prepared from the compound of Description 7 by an analogous procedure to that described in Example 32 using L-leucyl-L-alanine, methyl ester. The title compound was isolated as a hygroscopic foam.

EXAMPLE 38

N-[N-[3-Mercapto-2-(2-methylpropyl)-1-oxo-4-[(phenylmethoxy)carbonyl]butyl]-L-leucyl-L-alanine, methyl ester. (E38)

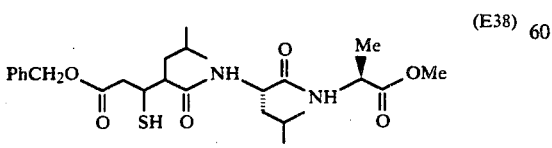

The title compound was prepared from the compound of Example 37 by an analogous procedure to that described in Example 10. The title compound was isolated as a mixture of diastereoisomers, (Isomer A/B, 1:1), m.p. 106°–110° C.

COLLAGENASE INHIBITOR ASSAY

The test is performed essentially as in Cawston and Barrett Anal. Biochem. 99, 340–345 (1979). Compounds for testing are dissolved in methanol and added to purified rabbit bone collagenase in buffer. After a 5–15 min incubation at 37° C., the assay tubes are cooled to 4° C. and $^{14}$C-acetylated rat skin Type I collagen is added. The assay tubes are incubated at 37° C. overnight. The $^{14}$C-collagen forms insoluble fibrils which are the substrate for the enzyme.

To terminate the assay, the assay tubes are spun at 12000 rpm for 15 min. Undigested $^{14}$C-collagen is pelleted, digested 14C-collagen is found as soluble peptides in the supernatant. A sample of the supernatant is taken for liquid scintillation counting.

The activity of collagenase inhibitors is expressed as that amount of compound which inhibits a known amount of enzyme by 50% (IC$_{50}$).

The activities of representative compound of the invention, in the above test procedure, are illustrated in the table below:

| Example No. | Isomer | IC$_{50}$ (nM) |
| --- | --- | --- |
| 2 | mixture of diastereoisomers | 100 |
| 2 | A | 3.9–6.4 (2 expts). |
| 2 | B | 72 |
| 4 | A | 31 |
| 4 | B | 270 |
| 4 | C | 230 |
| 4 | D | 12600 |
| 8 | A | 4.7–14 (3 expts.) |
| 10 | A | 8.3 |

We claim:

1. A compound of the formula (I) or a salt, solvate or hydrate thereof:

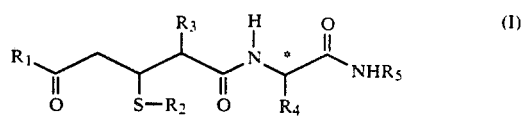

wherein

R$_1$ is —NR$_6$R$_7$ wherein each of R$_6$ and R$_7$ are hydrogen or alkyl; or R$_6$ and R$_7$ together with the nitrogen atom to which they are bonded form an N-morpholinyl or optionally nitrogen substituted piperazinyl ring;

R$_2$ is hydrogen;

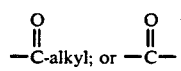

Z is optionally substituted aryl;

R$_3$ is C$_{3-6}$ alkyl;

R$_4$ is hydrogen; alkyl; —CH$_2$—R$_{10}$ where R$_{10}$ is optionally substituted phenyl or 5- or 6-membered monocyclic or 9- or 10-membered bicyclic heteroaryl containing one or two heteroatoms selected from nitrogen, oxygen, and sulfur which in the case of there being more than one heteroatom may be the same or different; or a group

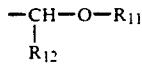

where $R_{11}$ is hydrogen; alkyl; or —$CH_2Ph$ is optionally substituted phenyl; $R_{12}$ is hydrogen or alkyl; and $R_5$ is hydrogen; alkyl; or a group

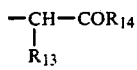

where $R_{13}$ is hydrogen; or alkyl; and $R_{14}$ is hydroxy; alkoxy; or —$NR_6R_7$ wherein each of $R_6$ and $R_7$ is hydrogen or alkyl; or $R_6$ and $R_7$ together with the nitrogen atom to which they are bonded form an N-morpholinyl or optionally nitrogen substituted piperazinyl ring.

2. A compound according to claim 1 wherein $R_{14}$ is selected from the group consisting of $N^1$-methyl-N-piperazinyl and N-morpholinyl.

3. A compound according to claim 1 wherein $R_1$ is selected from the group consisting of
$N^1$-methyl-N-piperazinyl and N-morphinyl;
$R_2$ is selected from the group consisting of hydrogen, acetyl, and benzoyl;
$R_3$ is selected from the group consisting of n-butyl, isobutyl and sec-butyl;
$R_4$ is selected from the group consisting of iso-butyl, benzyl, 4-methoxy benzyl, 1-(benzylkoxy)ethyl and 3-indolymethyl; and
$R_5$ is selected from the group consisting of hydrogen, methyl, and 1-(methoxycaronbyl)ethyl.

4. A compound according to claim 1, wherein $R_1$ is selected from the group consisting of N-piperazinyl, N-methyl-N-piperazinyl and N-morpholinyl;
$R_2$ is hydrogen, acetyl or benzyl;
$R_3$ is iso-butyl;
$R_4$ is benzyl or 4-methoxybenzyl; and
$R_5$ is methyl.

5. A compound according to claim 1 in which the chiral center marked with an asterisk in formula (I) has the S configuration.

6. A compound according to claim 1 which is selected from the group consisting of:
1-(3-Acetylmercapto-6-methyl-4-(((1-(S)(methylamino)-carbonyl)-2-(4-methoxyphenyl)ethyl-)amino)carbonyl)-heptanoyl)-4-methylpiperazine,
1-(3-Mercapto-6-methyl-4-(((1-(S)-(methylamino)-carbonyl)-2-(4-methoxyphenyl)ethyl)amino)carbonyl)-heptanoyl)-4-methylpiperazine,
1-(3-Acetylmercapto-6-methyl-4-(((1-(S)-(methylamino)-carbonyl)-2-(4 methoxyphenyl)ethyl-)amino)carbonyl)-heptanoyl) morpholine hydrate, and
1-(3-Mercapto-6-methyl-4-(((1-(S)-(methylamino)-carbonyl)-2-(4-methoxyphenyl)ethyl)amino)carbonyl)-heptanoyl) morpholine hemihydrate.

7. A pharmaceutical composition for use in treating collagenolytic conditions comprising an effective amount of compound according to claim 1 and a pharmaceutically acceptable carrier.

8. A method of treating collagenolytic conditions in mammals which comprises administering an effective amount of a compound according to claim 1 or a pharmaceutically acceptable salt, solvate or hydrate thereof, to a sufferer.

* * * * *